(12) United States Patent
Gozani et al.

(10) Patent No.: US 12,133,979 B2
(45) Date of Patent: Nov. 5, 2024

(54) "SMART" ELECTRODE ASSEMBLY FOR TRANSCUTANEOUS ELECTRICAL NERVE STIMULATION (TENS)

(71) Applicant: Neurometrix, Inc., Woburn, MA (US)

(72) Inventors: Shai N. Gozani, Newton, MA (US); Marc P. Cryan, Maynard, MA (US); Andres Aguirre, Belmont, MA (US); Glenn Herb, Weston, MA (US); Xuan Kong, Acton, MA (US)

(73) Assignee: Neurometrix, Inc., Woburn, MA (US)

( * ) Notice: Subject to any disclaimer, the term of this patent is extended or adjusted under 35 U.S.C. 154(b) by 299 days.

(21) Appl. No.: 17/590,049

(22) Filed: Feb. 1, 2022

(65) Prior Publication Data
US 2022/0226635 A1 Jul. 21, 2022

Related U.S. Application Data

(63) Continuation of application No. 15/853,044, filed on Dec. 22, 2017, now Pat. No. 11,235,142.
(Continued)

(51) Int. Cl.
*A61N 1/08* (2006.01)
*A61B 5/00* (2006.01)
(Continued)

(52) U.S. Cl.
CPC .......... *A61N 1/0456* (2013.01); *A61B 5/4806* (2013.01); *A61B 5/4809* (2013.01);
(Continued)

(58) Field of Classification Search
CPC .... A61N 1/0456; A61N 1/08; A61N 1/36021; A61N 1/025; A61N 1/36031;
(Continued)

(56) References Cited

U.S. PATENT DOCUMENTS

| 1,741,962 A | 12/1929 | Theodoropulos |
| 4,290,431 A | 9/1981 | Herbert et al. |

(Continued)

FOREIGN PATENT DOCUMENTS

| CN | 1665563 | 9/2005 |
| CN | 1919139 | 2/2007 |

(Continued)

OTHER PUBLICATIONS

Amazon, "Quell 2.0 Wearable Pain Relief Technology", Sep. 15, 2018.http:www.amazon.com/Quell-Wearable-Pain-Relief-Technology/dp/B07DHW2NJJ/ref—cm_cr_arp_d_product_top? ie=UTF8. Shown on p. 1, (Year: 2018).

(Continued)

Primary Examiner — Eugene T Wu
(74) Attorney, Agent, or Firm — Pandiscio & Pandiscio

(57) ABSTRACT

Apparatus for transcutaneous electrical nerve stimulation in a user, the apparatus comprising: a stimulation unit for electrically stimulating at least one nerve using electrical pulses; an electrode assembly connectable to the stimulation unit, the electrode assembly comprising a sensing unit, a storage unit, and a communications unit; and a control unit connected to the stimulation unit and the communications unit, the control unit being configured for controlling operation of the stimulation unit based on information from the electrode assembly.

14 Claims, 7 Drawing Sheets

Related U.S. Application Data

(60) Provisional application No. 62/438,914, filed on Dec. 23, 2016.

(51) Int. Cl.
*A61N 1/04* (2006.01)
*A61N 1/36* (2006.01)
*A61B 5/01* (2006.01)
*A61B 5/0533* (2021.01)
*A61B 5/11* (2006.01)
*A61N 1/02* (2006.01)

(52) U.S. Cl.
CPC ............ *A61N 1/08* (2013.01); *A61N 1/36021* (2013.01); *A61B 5/01* (2013.01); *A61B 5/0533* (2013.01); *A61B 5/1118* (2013.01); *A61B 5/4812* (2013.01); *A61B 5/4815* (2013.01); *A61B 2560/028* (2013.01); *A61N 1/025* (2013.01); *A61N 1/36031* (2017.08)

(58) Field of Classification Search
CPC .. A61N 1/3968; A61B 5/4806; A61B 5/4809; A61B 5/01; A61B 5/0533; A61B 5/1118; A61B 5/4812; A61B 5/4815; A61B 2560/028

See application file for complete search history.

(56) References Cited

U.S. PATENT DOCUMENTS

| | | |
|---|---|---|
| D263,869 S | 4/1982 | Sumiyasu |
| 4,503,863 A | 3/1985 | Katims |
| 4,605,010 A | 8/1986 | McEwen |
| 4,738,250 A | 4/1988 | Fulkerson et al. |
| 4,777,711 A | 10/1988 | Forkner et al. |
| 4,926,863 A | 5/1990 | Alt |
| 4,989,605 A | 2/1991 | Rossen |
| 5,048,523 A | 9/1991 | Yamasawa et al. |
| 5,063,929 A | 11/1991 | Bartelt et al. |
| D323,561 S | 1/1992 | Bartelt et al. |
| 5,121,747 A | 6/1992 | Andrews |
| 5,169,384 A | 12/1992 | Bosniak et al. |
| D342,571 S | 12/1993 | Givens, Sr. |
| D346,029 S | 4/1994 | Shalvi |
| 5,350,414 A | 9/1994 | Kolen |
| 5,429,589 A | 7/1995 | Cartmell et al. |
| 5,479,939 A | 1/1996 | Ogino |
| 5,487,759 A | 1/1996 | Bastyr et al. |
| 5,562,718 A | 10/1996 | Palermo |
| 5,806,522 A | 9/1998 | Katims |
| D411,887 S | 7/1999 | Agarwala |
| 5,919,149 A | 7/1999 | Allum |
| 5,948,000 A | 9/1999 | Larsen et al. |
| 5,954,758 A | 9/1999 | Peckham et al. |
| 6,033,370 A | 3/2000 | Reinbold et al. |
| 6,099,488 A | 8/2000 | Hung |
| 6,132,387 A | 10/2000 | Gozani et al. |
| 6,141,587 A | 10/2000 | Mower |
| 6,148,233 A | 11/2000 | Owen et al. |
| 6,161,044 A | 12/2000 | Silverstone |
| D443,362 S | 6/2001 | Storp |
| 6,266,558 B1 | 7/2001 | Gozani et al. |
| D450,313 S | 11/2001 | Koinuma |
| 6,430,450 B1 | 8/2002 | Bach-y-Rita et al. |
| D462,772 S | 9/2002 | Lamping et al. |
| 6,456,884 B1 | 9/2002 | Kenney |
| 6,507,755 B1 | 1/2003 | Gozani et al. |
| 6,611,789 B1 | 8/2003 | Darley |
| 6,662,051 B1 | 12/2003 | Eraker et al. |
| D484,984 S | 1/2004 | Takizawa et al. |
| D534,871 S | 1/2007 | Larsen |
| D541,042 S | 4/2007 | Andre et al. |
| D547,454 S | 7/2007 | Hsieh |
| D566,383 S | 4/2008 | Harris et al. |
| D584,414 S | 1/2009 | Lash et al. |
| D592,200 S | 5/2009 | Liu |
| D598,556 S | 8/2009 | Chen |
| D600,352 S | 9/2009 | Cryan |
| D607,198 S | 1/2010 | Andre et al. |
| D609,353 S | 2/2010 | Cryan |
| 7,668,598 B2 | 2/2010 | Herregraven et al. |
| D611,611 S | 3/2010 | Sachi et al. |
| D615,526 S | 5/2010 | Andre et al. |
| 7,720,548 B2 | 5/2010 | King |
| 7,725,193 B1 | 5/2010 | Chu |
| 7,787,946 B2 | 8/2010 | Stahmann et al. |
| D625,016 S | 10/2010 | Potts et al. |
| D625,829 S | 10/2010 | Arbesman et al. |
| D629,115 S | 12/2010 | Robertson |
| 7,887,493 B2 | 2/2011 | Stahmann et al. |
| D636,881 S | 4/2011 | Clemens et al. |
| D637,988 S | 5/2011 | Jinkinson |
| 8,108,049 B2 | 1/2012 | King |
| 8,121,702 B2 | 2/2012 | King |
| 8,131,374 B2 | 3/2012 | Moore et al. |
| D658,302 S | 4/2012 | Nixon |
| 8,284,070 B2 | 10/2012 | Chaudhari et al. |
| D677,792 S | 3/2013 | Vandiver |
| D680,735 S | 4/2013 | Itabashi et al. |
| 8,421,642 B1 | 4/2013 | McIntosh et al. |
| D687,951 S | 8/2013 | Della Torre et al. |
| D688,707 S | 8/2013 | Vincent et al. |
| D704,848 S | 5/2014 | Thomas et al. |
| D705,428 S | 5/2014 | Cheney et al. |
| D712,045 S | 8/2014 | Thornton |
| D712,052 S | 8/2014 | Thomas et al. |
| D713,049 S | 9/2014 | Shah |
| 8,825,175 B2 | 9/2014 | King |
| 8,849,407 B1 | 9/2014 | Danilov et al. |
| D716,457 S | 10/2014 | Brefka et al. |
| 8,862,238 B2 | 10/2014 | Rahimi et al. |
| D716,963 S | 11/2014 | Yosef et al. |
| 8,948,876 B2 | 2/2015 | Gozani et al. |
| D732,682 S | 6/2015 | Porat |
| D735,873 S | 8/2015 | Brefka et al. |
| 9,168,375 B2 | 10/2015 | Rahimi et al. |
| 9,173,581 B2 | 11/2015 | Boettcher et al. |
| D744,661 S | 12/2015 | Rizzi |
| D745,975 S | 12/2015 | Igaue et al. |
| D750,263 S | 2/2016 | Shigeno et al. |
| D750,798 S | 3/2016 | Yosef et al. |
| 9,282,287 B1 | 3/2016 | Marsh |
| 9,282,897 B2 | 3/2016 | Ross, Jr. et al. |
| D754,355 S | 4/2016 | Ganapathy et al. |
| D754,973 S | 5/2016 | Danze et al. |
| D757,292 S | 5/2016 | Chen |
| D758,605 S | 6/2016 | Chen |
| D758,606 S | 6/2016 | Chen |
| D759,262 S | 6/2016 | Chen |
| D759,263 S | 6/2016 | Chen |
| D759,958 S | 6/2016 | Requa |
| D762,628 S | 8/2016 | Yoon et al. |
| D762,872 S | 8/2016 | Chen |
| D767,775 S | 9/2016 | Gilmer et al. |
| 9,452,287 B2 | 9/2016 | Rosenbluth et al. |
| 9,474,898 B2 | 10/2016 | Gozani et al. |
| D774,654 S | 12/2016 | Anderson |
| D775,361 S | 12/2016 | Vosch et al. |
| D778,453 S | 2/2017 | Knaus et al. |
| D779,677 S | 2/2017 | Chen |
| 9,561,397 B2 | 2/2017 | Zaki |
| D784,544 S | 4/2017 | Dudkiewicz et al. |
| D784,546 S | 4/2017 | Gordon |
| D784,946 S | 4/2017 | Jun et al. |
| D788,056 S | 5/2017 | Choi et al. |
| 9,656,070 B2 | 5/2017 | Gozani et al. |
| D789,546 S | 6/2017 | Matfus et al. |
| D789,547 S | 6/2017 | Matfus et al. |
| D791,333 S | 7/2017 | Wilson |
| D792,363 S | 7/2017 | Kim et al. |
| 9,700,724 B2 | 7/2017 | Liu et al. |
| D794,331 S | 8/2017 | Grote |
| 9,731,126 B2 | 8/2017 | Ferree et al. |

(56) References Cited

U.S. PATENT DOCUMENTS

| | | |
|---|---|---|
| D798,170 S | 9/2017 | Toth et al. |
| D801,542 S | 10/2017 | Anderson |
| D802,780 S | 11/2017 | Hsu |
| 9,827,420 B2 | 11/2017 | Ferree et al. |
| D806,669 S | 1/2018 | Kangasmaa et al. |
| D810,311 S | 2/2018 | Chen |
| D810,843 S | 2/2018 | Karvandi |
| D810,952 S | 2/2018 | Hsu |
| D811,729 S | 3/2018 | Bysshe |
| D813,405 S | 3/2018 | Ho |
| D813,407 S | 3/2018 | Chen |
| D813,408 S | 3/2018 | Chen |
| D821,592 S | 6/2018 | Pham et al. |
| D828,569 S | 9/2018 | Mercuro |
| D829,182 S | 9/2018 | Li |
| 10,076,662 B2 | 9/2018 | Tuan |
| D830,565 S | 10/2018 | Xu |
| D831,017 S | 10/2018 | Choe et al. |
| D831,221 S | 10/2018 | Smith |
| D831,335 S | 10/2018 | Crease |
| D832,230 S | 10/2018 | Lee et al. |
| D834,719 S | 11/2018 | Theriot et al. |
| D836,788 S | 12/2018 | Peng |
| 10,154,922 B1 | 12/2018 | Perez et al. |
| D837,394 S | 1/2019 | Cryan et al. |
| 10,279,179 B2 | 5/2019 | Gozani et al. |
| 10,335,595 B2 | 7/2019 | Ferree et al. |
| D857,910 S | 8/2019 | Cryan et al. |
| D861,903 S | 10/2019 | Cryan et al. |
| D861,904 S | 10/2019 | Ho |
| D862,716 S | 10/2019 | Cryan et al. |
| D865,986 S | 11/2019 | Cryan et al. |
| D879,983 S | 3/2020 | Wang |
| 10,940,311 B2 | 3/2021 | Gozani et al. |
| 11,247,040 B2 | 2/2022 | Ferree et al. |
| 2002/0010497 A1 | 1/2002 | Merfeld et al. |
| 2003/0023192 A1 | 1/2003 | Foxlin |
| 2003/0074037 A1 | 4/2003 | Moore et al. |
| 2003/0114892 A1 | 6/2003 | Nathan et al. |
| 2003/0208246 A1 | 11/2003 | Kotlik et al. |
| 2004/0049241 A1 | 3/2004 | Campos |
| 2004/0122483 A1 | 6/2004 | Nathan et al. |
| 2004/0173220 A1 | 9/2004 | Harry et al. |
| 2005/0059903 A1 | 3/2005 | Izumi |
| 2005/0080463 A1 | 4/2005 | Stahmann et al. |
| 2005/0097970 A1 | 5/2005 | Nurse |
| 2005/0131317 A1 | 6/2005 | Oddsson et al. |
| 2005/0234525 A1 | 10/2005 | Phillips |
| 2005/0283204 A1 | 12/2005 | Buhlmann et al. |
| 2006/0052788 A1 | 3/2006 | Thelen et al. |
| 2006/0064037 A1 | 3/2006 | Shalon et al. |
| 2006/0085047 A1 | 4/2006 | Unsworth et al. |
| 2006/0085049 A1 | 4/2006 | Cory et al. |
| 2006/0089683 A1 | 4/2006 | Hagglof et al. |
| 2006/0095088 A1 | 5/2006 | De Ridder |
| 2006/0173507 A1 | 8/2006 | Mrva et al. |
| 2006/0190057 A1 | 8/2006 | Reese |
| 2006/0251334 A1 | 11/2006 | Oba et al. |
| 2007/0021786 A1 | 1/2007 | Parnis et al. |
| 2007/0060922 A1 | 3/2007 | Dreyfuss |
| 2007/0203435 A1 | 8/2007 | Novak |
| 2007/0203547 A1 | 8/2007 | Costello et al. |
| 2007/0276449 A1 | 11/2007 | Gunter et al. |
| 2008/0009772 A1 | 1/2008 | Tyler et al. |
| 2008/0077192 A1 | 3/2008 | Harry et al. |
| 2008/0146980 A1 | 6/2008 | Rousso et al. |
| 2008/0147143 A1 | 6/2008 | Popovic et al. |
| 2008/0147146 A1 | 6/2008 | Wahlgren et al. |
| 2008/0172102 A1 | 7/2008 | Shalev |
| 2008/0312709 A1 | 12/2008 | Volpe et al. |
| 2009/0030476 A1 | 1/2009 | Hargrove |
| 2009/0076364 A1 | 3/2009 | Libbus et al. |
| 2009/0082829 A1 | 3/2009 | Panken et al. |
| 2009/0082831 A1 | 3/2009 | Paul et al. |
| 2009/0112214 A1 | 4/2009 | Philippon et al. |
| 2009/0131993 A1 | 5/2009 | Rousso et al. |
| 2009/0203972 A1 | 8/2009 | Heneghan et al. |
| 2009/0240303 A1 | 9/2009 | Wahlstrand et al. |
| 2009/0264789 A1 | 10/2009 | Molnar et al. |
| 2009/0270947 A1 | 10/2009 | Stone et al. |
| 2009/0326604 A1 | 12/2009 | Tyler et al. |
| 2010/0004715 A1 | 1/2010 | Fahey |
| 2010/0010585 A1 | 1/2010 | Davis et al. |
| 2010/0042180 A1 | 2/2010 | Mueller et al. |
| 2010/0057149 A1 | 3/2010 | Fahey |
| 2010/0087903 A1 | 4/2010 | Van Herk et al. |
| 2010/0094103 A1 | 4/2010 | Kaplan et al. |
| 2010/0114257 A1 | 5/2010 | Torgerson |
| 2010/0131028 A1 | 5/2010 | Hsu et al. |
| 2010/0198124 A1 | 8/2010 | Bhugra |
| 2010/0217349 A1 | 8/2010 | Fahey |
| 2010/0241464 A1 | 9/2010 | Amigo et al. |
| 2010/0274304 A1 | 10/2010 | Wang et al. |
| 2011/0066209 A1 | 3/2011 | Bodlaender et al. |
| 2011/0106213 A1 | 5/2011 | Davis et al. |
| 2011/0166622 A1 | 7/2011 | Crosson et al. |
| 2011/0190594 A1 | 8/2011 | Heit et al. |
| 2011/0224665 A1 | 9/2011 | Crosby et al. |
| 2011/0245711 A1 | 10/2011 | Katra et al. |
| 2011/0257468 A1 | 10/2011 | Oser et al. |
| 2011/0264171 A1 | 10/2011 | Torgerson |
| 2011/0276107 A1 | 11/2011 | Simon et al. |
| 2011/0282164 A1 | 11/2011 | Yang et al. |
| 2012/0010680 A1 | 1/2012 | Wei et al. |
| 2012/0108998 A1 | 5/2012 | Molnar et al. |
| 2012/0123227 A1 | 5/2012 | Sun et al. |
| 2012/0130449 A1 | 5/2012 | Carlyon et al. |
| 2012/0303077 A1 | 11/2012 | De Vincentiis |
| 2012/0319816 A1 | 12/2012 | Al-Ali |
| 2013/0079846 A1 | 3/2013 | Single |
| 2013/0096641 A1 | 4/2013 | Strother et al. |
| 2013/0116514 A1 | 5/2013 | Kroner et al. |
| 2013/0158627 A1* | 6/2013 | Gozani ............... A61N 1/0456 607/46 |
| 2013/0197341 A1 | 8/2013 | Grob et al. |
| 2013/0217998 A1 | 8/2013 | Mahfouz et al. |
| 2013/0317333 A1 | 11/2013 | Yang et al. |
| 2014/0005759 A1 | 1/2014 | Fahey et al. |
| 2014/0039450 A1 | 2/2014 | Green et al. |
| 2014/0057232 A1 | 2/2014 | Wetmore et al. |
| 2014/0081353 A1 | 3/2014 | Cook et al. |
| 2014/0088192 A1 | 3/2014 | Heller et al. |
| 2014/0107729 A1 | 4/2014 | Sumners et al. |
| 2014/0163444 A1 | 6/2014 | Ingvarsson et al. |
| 2014/0188194 A1 | 7/2014 | Schepis et al. |
| 2014/0206976 A1 | 7/2014 | Thompson et al. |
| 2014/0221797 A1 | 8/2014 | Bailey et al. |
| 2014/0245784 A1 | 9/2014 | Proud et al. |
| 2014/0245791 A1 | 9/2014 | Proud et al. |
| 2014/0276236 A1 | 9/2014 | Swain et al. |
| 2014/0276549 A1 | 9/2014 | Osorio |
| 2014/0296934 A1 | 10/2014 | Gozani et al. |
| 2014/0296935 A1 | 10/2014 | Ferree et al. |
| 2014/0309709 A1 | 10/2014 | Gozani et al. |
| 2014/0336725 A1 | 11/2014 | Nogueira |
| 2014/0336730 A1 | 11/2014 | Simon et al. |
| 2014/0343625 A1 | 11/2014 | O Laighin |
| 2014/0371547 A1 | 12/2014 | Gartenberg et al. |
| 2014/0371814 A1 | 12/2014 | Spizzirri et al. |
| 2014/0379045 A1 | 12/2014 | Rahimi et al. |
| 2015/0012068 A1 | 1/2015 | Bradley et al. |
| 2015/0045853 A1 | 2/2015 | Alataris et al. |
| 2015/0100107 A1 | 4/2015 | Kiani et al. |
| 2015/0157242 A1 | 6/2015 | Sabesan |
| 2015/0157868 A1 | 6/2015 | Franke et al. |
| 2015/0174402 A1 | 6/2015 | Thomas et al. |
| 2015/0238094 A1 | 8/2015 | Lai et al. |
| 2015/0272511 A1 | 10/2015 | Najafi et al. |
| 2015/0306387 A1 | 10/2015 | Kong et al. |
| 2015/0321000 A1 | 11/2015 | Rosenbluth et al. |
| 2015/0328467 A1 | 11/2015 | Demers et al. |
| 2015/0335288 A1 | 11/2015 | Toth et al. |
| 2015/0335877 A1 | 11/2015 | Jeffery et al. |
| 2016/0007931 A1 | 1/2016 | Rubin et al. |

(56) References Cited

U.S. PATENT DOCUMENTS

| | | | |
|---|---|---|---|
| 2016/0029891 A1 | 2/2016 | Lin | |
| 2016/0113551 A1 | 4/2016 | Annegarn et al. | |
| 2016/0144174 A1 | 5/2016 | Ferree et al. | |
| 2016/0151628 A1 | 6/2016 | Simon et al. | |
| 2016/0166198 A1 | 6/2016 | Oddsson et al. | |
| 2016/0189371 A1 | 6/2016 | Krishna Rao et al. | |
| 2016/0213924 A1 | 7/2016 | Coleman et al. | |
| 2016/0235981 A1 | 8/2016 | Southwell et al. | |
| 2016/0242646 A1 | 8/2016 | Obma | |
| 2016/0243359 A1 | 8/2016 | Sharma | |
| 2016/0250464 A1 | 9/2016 | Zschaeck et al. | |
| 2016/0310730 A1 | 10/2016 | Martins et al. | |
| 2016/0367823 A1 | 12/2016 | Cowan et al. | |
| 2017/0043160 A1 | 2/2017 | Goodall et al. | |
| 2017/0056650 A1 | 3/2017 | Cohen et al. | |
| 2017/0080207 A1 | 3/2017 | Perez et al. | |
| 2017/0188864 A1 | 7/2017 | Drury | |
| 2017/0188872 A1 | 7/2017 | Hughes et al. | |
| 2017/0209693 A1 | 7/2017 | An et al. | |
| 2017/0224990 A1 | 8/2017 | Goldwasser et al. | |
| 2017/0238812 A1 | 8/2017 | Atlas | |
| 2017/0368345 A1 | 12/2017 | Kong et al. | |
| 2018/0000685 A1 | 1/2018 | Maloney et al. | |
| 2018/0028808 A1 | 2/2018 | Ferree et al. | |
| 2018/0132757 A1* | 5/2018 | Kong | A61B 5/1118 |
| 2018/0177996 A1 | 6/2018 | Gozani et al. | |
| 2018/0345014 A1 | 12/2018 | Gozani et al. | |
| 2019/0001135 A1 | 1/2019 | Yoo et al. | |
| 2019/0022372 A1 | 1/2019 | Dar et al. | |
| 2019/0022386 A1 | 1/2019 | Gozani et al. | |
| 2019/0134393 A1 | 5/2019 | Wong et al. | |
| 2020/0179694 A1 | 6/2020 | Kong et al. | |
| 2020/0219615 A1 | 7/2020 | Rabin et al. | |
| 2021/0128904 A1 | 5/2021 | Terekhov | |
| 2021/0260374 A1 | 8/2021 | Gozani et al. | |

FOREIGN PATENT DOCUMENTS

| | | |
|---|---|---|
| CN | 1926496 | 3/2007 |
| CN | 101557788 | 10/2009 |
| CN | 101626804 | 1/2010 |
| CN | 102202131 | 9/2011 |
| CN | 102355847 | 2/2012 |
| CN | 102740919 | 10/2012 |
| DE | 102010052710 | 5/2012 |
| EP | 0 971 653 | 1/2000 |
| EP | 1 985 277 | 2/2015 |
| JP | 61-171943 | 10/1986 |
| JP | 4-347140 | 12/1992 |
| JP | 9-117453 | 5/1997 |
| JP | 2000-167067 | 6/2000 |
| JP | 2005-34402 | 2/2005 |
| JP | 2005-81068 | 3/2005 |
| JP | 2006-68300 | 3/2006 |
| JP | 4185846 | 9/2008 |
| WO | WO 97/42999 | 11/1997 |
| WO | WO 99/64105 | 12/1999 |
| WO | WO 03/051453 | 6/2003 |
| WO | WO 2004/078132 | 9/2004 |
| WO | WO 2007/061746 | 5/2007 |
| WO | WO 2008/079757 | 7/2008 |
| WO | WO 2008/088985 | 7/2008 |
| WO | WO 2009/036313 | 3/2009 |
| WO | WO 2011/075179 | 6/2011 |
| WO | WO 2011/137193 | 11/2011 |
| WO | WO 2012/116407 | 9/2012 |
| WO | WO 2013/028960 | 2/2013 |
| WO | WO 2014/172381 | 10/2014 |
| WO | WO 2015/123373 | 8/2015 |
| WO | WO 2016/201366 | 12/2016 |
| WO | WO 2018/089655 | 5/2018 |
| WO | WO 2020/033883 | 2/2020 |

OTHER PUBLICATIONS

Amazon, "Quell Wearable Pain Relief Technology Starter Kit", Oct. 18, 2017. http://www.amazon.com/Quell-Wearable-ReliefTechnology-Starter/dp/B075YVCLZT/ref=cm_cr_arp_d_product_top?ie=UTF8. Shown on p. 1. (Year: 2017).

Amft, O. et al., Sensing Muscle Activities with Body-Worn Sensors, Conference Paper, May 2006.

Ancoli-Israel, S. .et al., The Role of Actigraphy in the Study of Sleep and Circadian Rhythms, Sleep, 2003, 26(3), p. 342-392.

Aurora, R. et al., The Treatment of Restless Legs Syndrome and Periodic Limb Movement Disorder in Adults—An Update for 2012: Practice Parameters with an Evidence-Based Systematic Review and Meta-Analyses, Sleep, 2012, vol. 35, No. 8, p. 1039-1062.

Barbarisi, Manlio et al., Pregabalin and Transcutaneous Electrical Nerve Stimulation for Postherpetic Neuralgia Treatment, The Clinical Journal of Pain, Sep. 2010;26(7):567-572.

Bifulco, P. et al., A Stretchable, Conductive Rubber Sensor to Detect Muscle Contraction for Prosthetic Hand Control, The 6th IEEE International Conference on E-Health and Bioengineering—EHB 2017, Jun. 22-24, 2017, pp. 173-176.

Bjordal JM et al., Transcutaneous electrical nerve stimulation (TENS) can reduce postoperative analgesic consumption. A meta-analysis with assessment of optimal treatment parameters for postoperative pain, European Journal of Pain, 2003, vol. 7(2): 181-188.

Bloodworth DM et al., Comparison of stochastic vs. conventional transcutaneous electrical stimulation for pain modulation in patients with electromyographically documented radiculopathy, American Journal of Physical Medicine & Rehabilitation, 2004, vol. 83(8): 584-591.

Bonnet, M. et al., Recording and Scoring Leg Movements, Sleep, 1993, vol. 16, No. 8, p. 748-759.

Boyle, J. et al., Randomized, Placebo-Controlled Comparison of Amitriptyline, Duloxetine, and Pregabalin in Patients With Chronic Diabetic Peripheral Neuropathic Pain, Diabetes Care, 2012, vol. 35, p. 2451-2458.

Chandran P et al., Development of opioid tolerance with repeated transcutaneous electrical nerve stimulation administration, Pain, 2003, vol. 102: 195-201.

Chen CC et al., A. comparison of transcutaneous electrical nerve stimulation (TENS) at 3 and 80 pulses per second on cold-pressor pain in healthy human participants, Clinical Physiology and Functioning Imaging, 2010, vol. 30(4): 260-268.

Chen CC et al., An investigation into the effects of frequency-modulated transcutaneous electrical nerve stimulation (TENS) on experimentally-induced pressure pain in healthy human participants, The Journal of Pain, 2009, vol. 10(10): 1029-1037.

Chen CC et al., Differential frequency effects of strong nonpainful transcutaneous electrical nerve stimulation on experimentally induced ischemic pain in healthy human participants, The Clinical Journal of Pain, 2011, vol. 27(5): 434-441.

Chen CC et al., Does the pulse frequency of transcutaneous electrical nerve stimulation (TENS) influence hypoalgesia? A systematic review of studies using experimantal pain and healthy human participants, Physiotherapy, 2008, vol. 94: 11-20.

Claydon LS et al., Dose-specific effects of transcutaneous electrical nerve stimulation on experimental pain, Clinical Journal of Pain, 2011, vol. 27(7): 635-647.

Cole, R.J. et al., Automatic Sleep/Wake Identification From Wrist Activity, Sleep, 1992, 15(5), p. 461-469.

Cruccu G. et al., EFNS guidelines on neurostimulation therapy for neuropathic pain, European Journal of Neurology, 2007, vol. 14: 952-970.

Dailey DL et al., Transcutaneous Electrical Nerve Stimulation (TENS) Reduces Pain, Fatigue, and Hyperalgesia while Restoring Central Inhibition in Primary Fibromyalgia, Pain, Nov. 2013, vol. 154, No. 11, pp. 2554-2562.

Dailey, D. et al., Transcutaneous Electrical Nerve Stimulation Reduces Movement-Evoked Pain and Fatigue: A Randomized, Controlled Trial, Arthritis & Rheumatology, May 2020, vol. 72, No. 5, pp. 824-836.

Davies Hto et al., Diminishing returns or appropriate treatment strategy? —an analysis of short-term outcomes after pain clinic treatment, Pain, 1997, vol. 70: 203-208.

(56) References Cited

OTHER PUBLICATIONS

Desantana JM et al., Effectiveness of transcutaneous electrical nerve stimulation for treatment of hyperalgesia and pain, Curr Rheumatol Rep. 2008, vol. 10(6): 492-499.
Dubinsky RM et al., Assessment: Efficacy of transcutaneous electric nerve stimulation in the treatment of pain in neurologic disorders (an evidence-based review): Report of the therapeutics and technology assessment subcommittee of the american academy of neurology, Neurology, 2010, vol. 74: 173-176.
Fary Re et al., Monophasic electrical stimulation produces high rates of adverse skin reactions in healthy subjects, Physiotherapy Theory and Practice, 2011, vol. 27(3): 246-251.
Fishbain, David A. et al. Does Pain Mediate the Pain Interference with Sleep Problem in Chronic Pain? Findings from Studies for Management of Diabetic Peripheral Neuropathic Pain with Duloxetine, Journal of Pain Symptom Management, Dec. 2008; 36(6): 639-647.
Fishbain, David A. et al., Transcutaneous Electrical Nerve Stimulation (TENS) Treatment Outcome in Long-Term Users, The Clinical Journal of Pain, Sep. 1996; 12(3):201-214.
Food and Drug Administration, Draft Guidance for Industry and Staff: Class II Special Controls Guidance Document: Transcutaneous Electrical Nerve Stimulator for Pain Relief, Apr. 5, 2010.
Garrison DW et al., Decreased activity of spontaneous and noxiously evoked dorsal horn cells during transcutaneous electrical nerve stimulation (TENS), Pain, 1994, vol. 58: 309-315.
Gilron, I. et al., Chronobiological Characteristics of Neuropathic Pain: Clinical Predictors of Diurnal Pain Rhythmicity, The Clinical Journal of Pain, 2013.
Gozani SN et al., Fixed-Site High-Frequency Transcutaneous Electrical Nerve Stimulation for Treatment of Chronic Low Back and Lower Extremity Pain, Journal of Pain Research, 2016, vol. 9, pp. 469-479.
Hausdorff, J.M. et al., Gait Variability and Fall Risk in Community-Living Older Adults: A 1-Year Prospective Study, Arch Phys Med Rehabil, Aug. 2001, vol. 82, pp. 1050-1056.
Hori, T. et al., Skin Potential Activities and Their Regional Differences During Normal Sleep In Humans, The Japanese Journal of Physiology, 1970, vol. 20, p. 657-671.
Jelinek HF et al., Electric pulse frequency and magnitude of perceived sensation during electrocutaneous forearm stimulation, Arch Phys Med Rehabil, 2010, vol. 91: 1372-1382.
Jin DM et al., Effect of transcutaneous electrical nerve stimulation on symptomatic diabetic peripheral neuropathy: a meta-analysis of randomized controlled trials, Diabetes Research and Clinical Practice, 2010, vol. 89: 10-15.
Johnson MI et al., Analgesic effects of different frequencies of transcutaneous electrical nerve stimulation on cold-induced pain in normal subjects, Pain, 1989, vol. 39: 231-236.
Johnson MIi et al., Transcutaneous Electrical Nerve Stimulation (TENS) and TENS-like devices: do they provide pain relief?, Pain Reviews, 2001, vol. 8: 7-44.
Johnson Mi et al., Transcutaneous electrical nerve stimulation for the management of painful conditions: focus on neuropathic pain, Expert Review of Neurotherapeutics, 2011, vol. 11(5): 735-753.
Johnson, M.I. et al., An in-depth study of long-term users of transcutaneous electrical nerve stimulation (TENS). Implications for clinical use of TENS. Pain. Mar. 1991;44(3):221-229.
Kaczmarek, Kurt A. et al . . . Electrotactile and Vibrotactile Displays for Sensory Substitution Systems. IEEE Trans. Biomed. Eng. Jan. 1991;38 (1):1-16.
Kantor G et al., The effects of selected stimulus waveforms on pulse and phase characteristics at sensory and motor thresholds, Physical Therapy, 1994, vol. 74(10): 951-962.
Keller, Thierry et al., Electrodes for transcutaneous (surface) electrical stimulation. J. Automatic Control, University of Belgrade. 2008; 18(2):35-45.
Koumans, A. J. R. et al., Electrodermal Levels and Fluctuations During Normal Sleep, Psychophysiology, 1968, 5(3), p. 300-306.
Kovacevic-Ristanovic, R. et al., Nonpharmacologic Treatment of Periodic Leg Movements in Sleep, Arch. Phys. Med. Rehabil., 1991, vol. 72, p. 385-389.
Kripke, D.F. et al., Wrist Actigraphic Scoring for Sleep Laboratory Patients: Algorithm Development, Journal of Sleep Research, 2010, 19(4), p. 612-619.
Law Ppw et al., Optimal stimulation frequency of transcutaneous electrical nerve stimulation on people with knee osteoarthritis, J Rehabil Med, 2004, vol. 36: 220-225.
Leonard G et al., Deciphering the role of endogenous opioids in high-frequency TENS using low and high doses of naloxone, Pain, 2010, vol. 151: 215-219.
Levy et al., A comparison of two methods for measuring thermal thresholds in diabetic neuropathy, Journal of Neurology, Neurosurgery, and Psychiatry, 1989, vol. 52: 1072-1077.
Lopes, L. et al., Restless Legs Syndrome and Quality of Sleep in Type 2 Diabetes, Diabetes Care, 2005, vol. 28, No. 11, p. 2633-2636.
Lykken, D.T., Properties of Electrodes Used in Electrodermal Measurement. J. Comp. Physiol. Psychol. Oct. 1959; 52:629-634.
Lykken, D.T., Square-Wave Analysis of Skin Impedance. Psychophysiology. Sep. 1970; 7(2):262-275.
MacFarlane, T. et al., Whether the weather influences pain? Results from EpiFunD study in North West England, Rheumatology, 2010, vol. 49, pp. 1513-1520.
Melzack R et al., Pain mechanisms: A New Theory, Science, 1965, vol. 150(3699): 971-979.
Moran F et al., Hypoalgesia in response to transcutaneous electrical nerve stimulation (TENS) depends on stimulation intensity, The Journal of Pain, 2011, vol. 12(8): 929-935.
Nightingale, S., The neuropathic pain market, Nature Reviews, 2012, vol. 11, p. 101-102.
Okamoto-Mizuno. K. et al., Effects of thermal environment on sleep and circadian rhythm, Journal of Physiological Anthropology, 2012, vol. 31, No. 14, pp. 1-9.
Oosterhof, Jan et al., Outcome of transcutaneous electrical nerve stimulation in chronic pain: short-term results of a double-blind, randomised, placebo-controlled trial. J. Headache Pain. Sep. 2006; 7 (4):196-205.
Oosterhof, Jan et al., The long-term outcome of transcutaneous electrical nerve stimulation in the treatment for patients with chronic pain: a randomized, placebo-controlled trial. Pain Pract. Sep. 2012; 12(7):513-522.
Ossipov MH et al., Central Modulation of Pain, The Journal of Clinical Investigation, Nov. 2010, vol. 120, No. 11, pp. 3779-3787.
Pantaleao Ma et al., Adjusting pulse amplitude during transcutaneous electrical nerve stimulation (TENS) application produces greater hypoalgesia, The Journal of Pain, 2011, vol. 12(5):581-590.
Paquet, J. et al., Wake Detection Capacity of Actigraphy During Sleep, Sleep, 2007, 30(10), p. 1362-1369.
Pieber K et al., Electrotherapy for the treatment of painful diabetic peripheral neuropathy: a review, Journal of Rehabilitation Medicine, 2010, vol. 42: 289-295.
Raskin, J. et al., A Double-Blind, Randomized Multicenter Trial Comparing Duloxetine with Placebo in the Management of Diabetic Peripheral Neuropathic Pain, Pain Medicine, 2005, 6(5), p. 346-356.
Sadeh, A., The Role and Validity of Actigraphy in Sleep Medicine: An Update, Sleep Medicine Reviews, 2011, vol. 15, p. 259-267.
Sadosky, A. et al., Burden of Illness Associated with Painful Diabetic Peripheral Neuropathy Among Adults Seeking Treatment in the US: Results from a Retrospective Chart Review and Cross-Sectional Survey, Diabetes, Metabolic Syndrome and Obesity: Targets and Therapy, 2013, vol. 6, p. 79-92.
Sano, A. et al., Quantitative analysis of wrist electrodermal activity during sleep, International Journal of Psychophysiology, 2014, vol. 94, pp. 382-389.
Scherder, E. J. A. et al., Transcutaneous Electrical Nerve Stimulation (TENS) Improves the Rest-Activity Rhythm in Midstage Alzheimer's Disease, Behavioral Brain Research, 1999, vol. 101, p. 105-107.
Sheridan et al., Some Factors Influencing the Threshold of the Electrocutaneous Stimulus, Perceptual and Motor Skills, 1966, vol. 22, pp. 647-654.

(56) References Cited

OTHER PUBLICATIONS

Susi et al., Motion Mode Recognition and Step Detection Algorithms for Mobile Phone Users, Sensors, Jan. 24, 2013, vol. 13, pp. 1539-1562.

Taborri et al., A Novel HMM Distributed Classifier for the Detection of Gait Phases by Means of a Wearable Inertial Sensor Network, Sensors, Sep. 2014, vol. 14, pp. 16212-16234.

Timmermans, E. et al., Self-perceived weather sensitivity and joint pain in older people with osteoarthritis in six European countries: results from the European Project on OSteoArthritis (EPOSA), BMC Musculoskeletal Disorders, 2014, vol. 15, No. 66, pp. 1-11.

Tryon, W. W., Issues of Validity in Actigraphic Sleep Assessment, Sleep, 2004, 27(1), p. 158-165.

Tsai, Y. et al., Impact of Subjective Sleep Quality on Glycemic Control in Type 2 *Diabetes Mellitus*, Family Practice, 2012, vol. 29, p. 30-35.

Van Boxtel, A., Skin resistance during square-wave electrical pulses of 1 to 10 mA. Med. Biol. Eng. Comput. Nov. 1977; 15(6):679-687.

Van Someren, E. J. W. et al., Gravitational Artefact in Frequency Spectra of Movement Acceleration: Implications for Actigraphy in Young and Elderly Subjects, Journal of Neuroscience Methods, 1996, vol. 65, p. 55-62.

Vance et al., Using TENS for pain control: the state of the evidence, Pain Management, 2014, vol. 4, No. 3, pp. 197-209.

Waeber, R. et al., Biosection Search with Noisy Responses, SIAM J. Control Optim., 2013, vol. 51, No. 3, pp. 2261-2279.

Webster, J. B. et al., An Activity-Based Sleep Monitor System for Ambulatory Use, Sleep, 1982, 5(4), p. 389-399.

Zelman, D. C. et al., Sleep Impairment in Patients With Painful Diabetic Peripheral Neuropathy, The Clinical Journal of Pain, 2006, 22(8), p. 681-685.

Zucconi, M. et al., The official World Association of Sleep Medicine (WASM) standards for recording and scoring periodic leg movements in sleep (PLMS) and wakefulness (PLMW) developed in collaboration with a task force from the International Restless Legs Syndrome Study Group (IRLSSG), Sleep Medicine, 2006, vol. 7, p. 175-183.

Mallik et al., Nerve Conduction Studies: Essentials and Pitfalls in Practice, Neurol Neurosurg Psychiatry, 2005, ii23-ii31.

\* cited by examiner

"SMART" ELECTRODE ASSEMBLY FOR TRANSCUTANEOUS ELECTRICAL NERVE STIMULATION (TENS)

REFERENCE TO PENDING PRIOR PATENT APPLICATIONS

This patent application is a continuation of U.S. patent application Ser. No. 15/853,044, filed Dec. 22, 2017 by Neurometrix for "SMART" ELECTRODE ASSEMBLY FOR TRANSCUTANEOUS ELECTRICAL NERVE STIMULATION (TENS), which patent application claims benefit of prior U.S. Provisional Patent Application Ser. No. 62/438,914, filed Dec. 23, 2016 by Neurometrix, Inc. and Shai N. Gozani et al. for SMART ELECTRODE FOR TRANSCUTANEOUS ELECTRICAL NERVE STIMULATION.

The two (2) above-identified patent applications are hereby incorporated herein by reference.

FIELD OF THE INVENTION

This invention relates generally to Transcutaneous Electrical Nerve Stimulation (TENS) devices that deliver electrical currents across the intact skin of a user via electrodes to provide symptomatic relief of pain. More specifically, this invention relates to apparatus and methods to manage utilization of the electrodes used in TENS therapy and to control stimulation for delivering pain-relieving therapy.

BACKGROUND OF THE INVENTION

Transcutaneous electrical nerve stimulation (TENS) is the delivery of electricity (i.e., electrical stimulation) across the intact surface of a user's skin in order to activate sensory nerve fibers. The most common application of TENS therapy is to provide analgesia, such as for the alleviation of chronic pain. Other applications of TENS therapy include, but are not limited to, reducing the symptoms of restless leg syndrome, decreasing nocturnal muscle cramps, and providing relief from generalized pruritus. Electrical stimulation is delivered to the body tissue through electrode-skin interfaces created when electrodes are placed in contact with the skin.

A conceptual model for how sensory nerve stimulation leads to pain relief was proposed by Melzack and Wall in 1965. Their theory proposes that the activation of sensory nerves (Aβ fibers) closes a "pain gate" in the spinal cord that inhibits the transmission of pain signals carried by nociceptive afferents (C and Aδ fibers) to the brain. In the past 20 years, anatomic pathways and molecular mechanisms that may underlie the pain gate have been identified. Sensory nerve stimulation (e.g., via TENS) activates the descending pain inhibition system, primarily the periaqueductal gray (PAG) and rostroventral medial medulla (RVM) located in the mid-brain and medulla sections of the brain stem, respectively. The PAG has neural projections to the RVM, which in turn has diffuse bilateral projections into the spinal cord dorsal horn that inhibit ascending pain signal transmission.

Electrical stimulation is delivered to the body tissue through electrode-skin interfaces created when electrodes are placed in contact with the skin. TENS is typically delivered in short discrete pulses, with each pulse typically being several hundred microseconds in duration, at frequencies between about 10 and 150 Hz, through hydrogel electrode pads placed in direct contact with the user's skin.

To allow effective stimulation, good electrode-skin interface conditions need to be maintained. Many factors may affect the electrode-skin interface conditions. These factors include skin conditions such as dryness of the skin and temperature of the skin. Factors such as electrode on-skin time and TENS stimulation duration and intensity may also affect the rate of degradation of the electrode-skin interface conditions. Poor electrode-skin interface conditions may lead to inadequate electrical stimulation of the nerves, thus compromising the effectiveness of TENS therapy.

To ensure adequate electrode-skin interface conditions, TENS users often replace their TENS electrodes at a fixed time interval. While replacing the TENS electrodes at a fixed time interval may work for a majority of users, it may not be appropriate for some users who might have a drier-than-average skin condition or who might use the TENS electrodes less frequently during a particular period of time. Therefore, there is a need for a "smart" TENS electrode assembly to overcome these limitations.

Additionally, TENS therapy is delivered to relieve chronic pain. Certain users find it helpful to receive TENS therapy during the day and throughout the night. Chronic pain is known to interfere with sleep, and TENS therapy at night can reduce the pain and minimize its interference with sleep. Fixed TENS therapy dosages (in terms of the onset, duration, and intensity of the electrical stimulation) may not be appropriate for all nights, inasmuch as sleep quality and sleep patterns may vary from night to night. Therefore, there is also a need for a "smart" TENS electrode assembly to facilitate accurate sleep monitoring in order to tailor TENS therapy dosages based on actual sleep patterns each night.

Furthermore, it has been found that electrical stimulation intensity needs to be set at a level which evokes a strong but comfortable sensation in order for most chronic pain sufferers to receive the maximum TENS therapy benefit. The target stimulation intensity level $I_T$ (resulting in a strong but comfortable sensation) may change with time for each user. The changes in the target stimulation intensity level may be related to circadian rhythm (e.g., time of day) or longer term trends (e.g., disease progression) or environmental conditions (e.g., weather), etc. Manual adjustment of the target stimulation intensity level can be inconvenient or impractical for some users. There is, therefore, a need to develop a "smart" TENS electrode assembly that can measure the effect of stimulation to facilitate automated TENS stimulation intensity adjustment in real time to maximize the effectiveness of every TENS therapy session.

In addition to the foregoing, modern electronics and intelligent algorithms have enabled TENS therapy settings to be more precise and personalized. Any variations in the TENS electrodes (e.g., in terms of their materials, sizes, shapes, etc.) could affect the intended delivery of electrical stimulation to the user. Therefore, there is also a need for a "smart" TENS electrode assembly that can uniquely identify its manufacturing origin, materials used, size, shape, and other characteristics that may affect the transmittal of electrical current into the body of the user via the electrode-skin interfaces.

SUMMARY OF THE INVENTION

The present invention comprises a novel "smart" electrode assembly comprising one or more conductive hydrogel electrode pads disposed on a layer of supporting material (i.e., a substrate) so as to form the "smart" electrode assembly. Each hydrogel electrode pad is electronically connected to a TENS stimulator via a connector. Integrated circuit (IC)

components are placed on either (or both) sides of the supporting material (i.e., the substrate) which carries the conductive hydrogel electrode pads. Sensors of various types (e.g., thermal sensors, chemical sensors, moisture sensors, force sensors, accelerometers, gyroscopes, etc.) are also placed on either (or both) sides of the supporting material (i.e., the substrate) which carries the conductive hydrogel electrode pads. Data from the sensors is communicated directly to the TENS stimulator or stored on the IC components (carried by the supporting material) and later transmitted to the TENS stimulator. The IC components also store information characterizing various physical (e.g., size, shape, material composition, etc.) and temporal (e.g., date of manufacture, duration of use, etc.) aspects of the "smart" electrode assembly. Other information stored in the IC components may also include intended region or country of use (e.g., United States, European Union, China, etc.) to comply with regulatory requirements. Information stored in the IC components is also communicated to the TENS stimulator. The TENS stimulator integrates the information from one or more of the aforementioned sources and uses that information to modify stimulation settings, to alter behavior of the sensors, and/or to update the memory contents of the IC components. Note that the TENS stimulator can also use information from sources other than the on-board sensors and IC components to modify stimulation parameters, e.g., the TENS stimulator may also use user feedback, external information sources such as weather station forecasts, etc. to modify stimulation parameters.

The TENS stimulator can be permanently or releasably mounted on the layer of supporting material (i.e., the substrate) of the "smart" electrode assembly, or the layer of supporting material (i.e., the substrate) of the "smart" electrode assembly can be permanently or releasably mounted to the TENS stimulator. Regardless of the manner in which the TENS stimulator and the "smart" electrode assembly are mounted to one another, the TENS stimulator is electrically connected to the one or more conductive hydrogel electrode pads of the "smart" electrode assembly. Additionally, the TENS stimulator is configured to communicate with the components mounted to the layer of supporting material (i.e., the substrate) of the "smart" electrode assembly (e.g., the IC components, the sensors, etc.) with both read and write capabilities. Communications can be carried out in either an encrypted or unencrypted manner.

In one preferred form of the invention, there is provided apparatus for transcutaneous electrical nerve stimulation in a user, said apparatus comprising:
    a stimulation unit for electrically stimulating at least one nerve using electrical pulses;
    an electrode assembly connectable to said stimulation unit, said electrode assembly comprising a sensing unit, a storage unit, and a communications unit; and
    a control unit connected to said stimulation unit and said communications unit, said control unit being configured for controlling operation of said stimulation unit based on information from said electrode assembly.

In another preferred form of the invention, there is provided apparatus for transcutaneous electrical nerve stimulation in a user, said apparatus comprising:
    a stimulation unit for electrically stimulating at least one nerve using electrical pulses;
    an electrode assembly connectable to said stimulation unit, said electrode assembly comprising a sensing unit and a communications unit;
    a sleep determination unit configured to analyze sleep characteristics of the user; and
    a control unit connected to said stimulation unit, said communications unit, and said sleep determination unit, said control unit being configured for controlling operation of said stimulation unit.

In another preferred form of the invention, there is provided a method for transcutaneous electrical nerve stimulation in a user, said method comprising the steps of:
    applying an electrode assembly to the body of the user;
    connecting a stimulation unit to said electrode assembly;
    measuring at least one characteristic of at least one of said electrode assembly and the user;
    determining stimulation parameters based on said at least one measured characteristic; and
    stimulating at least one nerve using said stimulation parameters.

In another preferred form of the invention, there is provided a method for transcutaneous electrical nerve stimulation in a user, said method comprising the steps of:
    applying an electrode assembly to the body of the user;
    connecting a stimulation unit to said electrode assembly;
    measuring at least one characteristic of at least one of said electrode assembly and the user; and
    communicating the status of said electrode assembly to the user.

In another preferred form of the invention, there is provided a method for transcutaneous electrical nerve stimulation in a user, said method comprising the steps of:
    applying an electrode assembly to the body of the user;
    connecting a stimulation unit to said electrode assembly;
    measuring at least one property of the user to determine sleep characteristics of the user;
    modifying stimulation parameters based on said determined sleep characteristics of the user; and
    stimulating at least one nerve using said stimulation parameters.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein.

DETAILED DESCRIPTION OF THE PREFERRED EMBODIMENTS

The TENS Device in General

The present invention comprises the provision and use of a novel TENS device which comprises a TENS stimulator designed to be placed on a user's upper calf (or other anatomical location) and a "smart" electrode assembly designed to apply electrical stimulation from the TENS stimulator to at least one nerve disposed in the user's upper calf (or other anatomical location). A key feature of the present invention is that the "smart" electrode assembly measures and tracks factors such as skin temperature, skin condition (e.g., dryness), electrode on-skin time, electrode usage period, electrode-skin impedance, etc. These factors, together with manufacturer specifications such as material composition and the geometry of the hydrogel electrode pads of the "smart" electrode assembly, can impact the quality and life span of the "smart" electrode assembly which delivers the electrical stimulation current to the user for TENS therapy.

Figure 1:
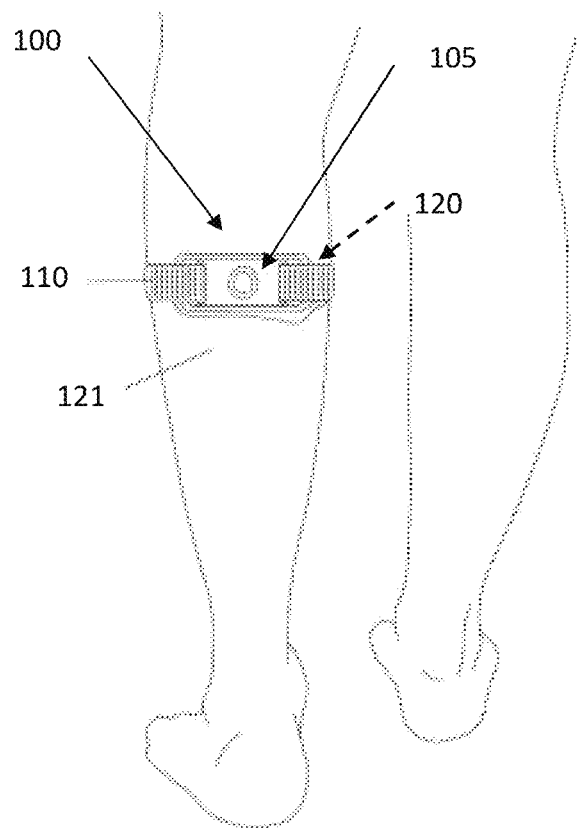
FIG. 1 is a schematic view showing a novel TENS device with a novel "smart" electrode assembly formed in accordance with the present invention, wherein the novel TENS device is mounted to the upper calf of a user.

More particularly, and looking now at FIG. 1, there is shown a novel TENS device 100 formed in accordance with the present invention, with novel TENS device 100 comprising a TENS stimulator 105, a strap 110, and a "smart" electrode assembly 120, with novel TENS device 100 being shown worn on a user's upper calf 121. Smart electrode assembly 120 is disposed on the rear side of TENS stimulator 105 and strap 110 so that the smart electrode assembly is "underneath" the TENS stimulator and strap in FIG. 1. A user may wear TENS device 100 on one leg or on both legs (either one at a time or simultaneously), or a user may wear a TENS device 100 on another area of the body separate from, or in addition to, a TENS device 100 worn on one leg (or both legs) of the user.

Figure 2:
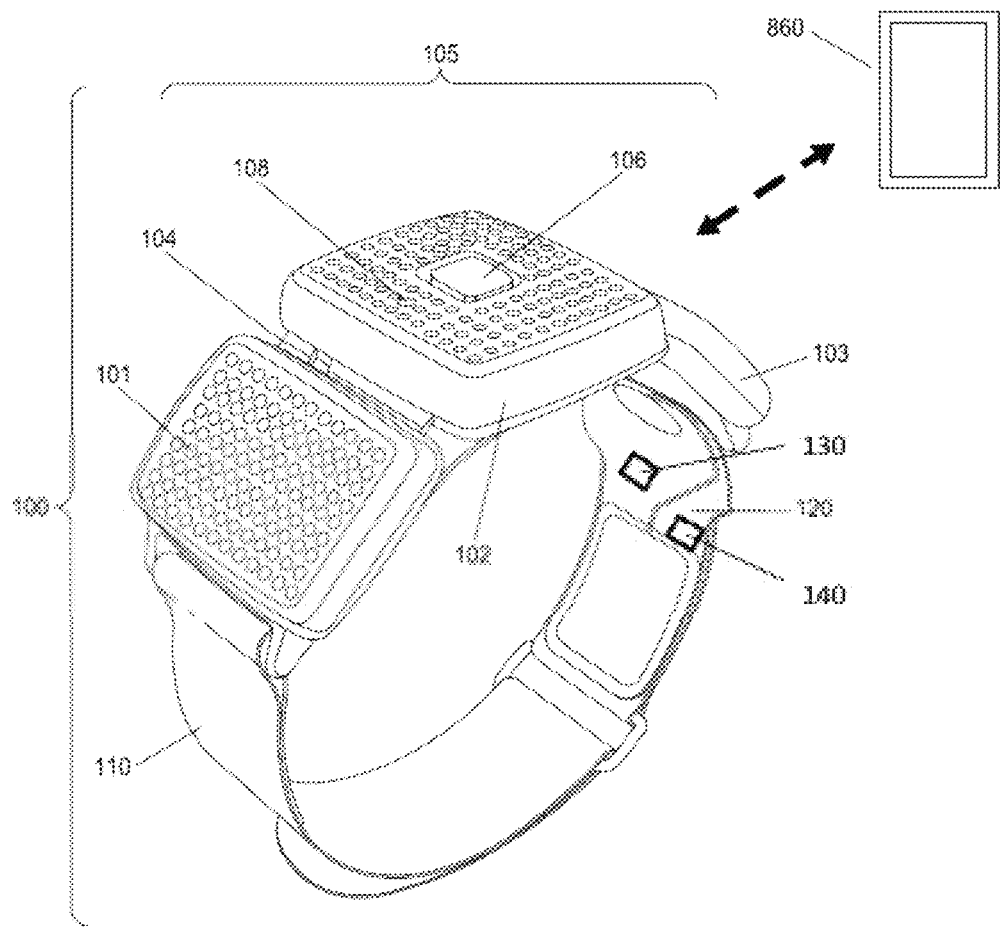
FIG. 2 is a schematic view showing the novel TENS device with the novel "smart" electrode assembly of FIG. 1 in greater detail.

Looking next at FIG. 2, TENS device 100 is shown in greater detail. TENS device 100 preferably comprises the aforementioned three components: stimulator 105, strap 110, and smart electrode assembly 120 (comprising, as will hereinafter be discussed, at least one cathode electrode and at least one anode electrode appropriately electrically connected to TENS stimulator 105). As shown in FIG. 2, TENS stimulator 105 may comprise three mechanically and electrically interconnected compartments 101, 102, and 103. Compartments 101, 102, 103 are preferably interconnected by hinge mechanisms 104 (only one of which is visible in FIG. 2), thereby allowing TENS device 100 to conform to the curved anatomy of a user's leg. In a preferred embodiment of the present invention, compartment 102 houses the TENS stimulation circuitry (except for a battery) and user interface elements 106 and 108.

In one preferred form of the invention, compartments 101 and 103 are smaller auxiliary compartments that house a battery for powering the TENS stimulation circuitry and other circuitry, and other ancillary elements, such as a wireless interface unit (not shown) of the sort well known in the art for allowing TENS device 100 to wirelessly communicate with other elements (e.g., a hand-held electronic device 860, such as a smartphone, see FIG. 2).

In another form of the invention, only one or two compartments may be used for housing all of the TENS stimulation circuitry, battery, and other ancillary elements of the present invention.

In another form of the invention, a greater number of compartments may be used, e.g., to enable TENS device 100 to better conform to the body and to improve user comfort.

And in still another form of the invention, a flexible circuit board is used to distribute the TENS stimulation circuitry and other circuitry more evenly around the leg of the user and thereby reduce the thickness of the device.

Still looking at FIG. 2, interface element 106 preferably comprises a push button for user control of electrical stimulation by TENS device 100, and interface element 108 preferably comprises an LED for indicating stimulation status and providing other feedback to the user. Although a single LED is shown in FIG. 2, interface element 108 may comprise multiple LEDs with different colors. A wireless interface unit (not shown) of the sort well known in the art is preferably incorporated in compartment 102 to allow TENS device 100 to wirelessly communicate with other elements (e.g., a hand-held electronic device 860 such as a smartphone) as another form of user interface. Additional user interface elements (e.g., an LCD display, audio feedback through a beeper or voice output, haptic devices such as a vibrating element, etc.) are also contemplated and are considered to be within the scope of the present invention.

In one preferred form of the invention, TENS device 100 is configured to be worn on the user's upper calf 121 as shown in FIG. 1, although it should also be appreciated that TENS device 100 may be worn on other anatomical locations, or multiple TENS devices 100 may be worn on various anatomical locations, etc. TENS device 100 (comprising the aforementioned TENS stimulator 105, strap 110, and smart electrode assembly 120) is secured to upper calf 121 (or other anatomical location) of the user by placing the apparatus in position against the upper calf (or other anatomical location) and then tightening strap 110. More particularly, in one preferred form of the invention, smart electrode assembly 120 is deliberately sized and configured so that it will apply appropriate electrical stimulation to the appropriate anatomy of the user regardless of the specific rotational position of TENS device 100 on the leg (or other anatomical location) of the user.

Figure 3:
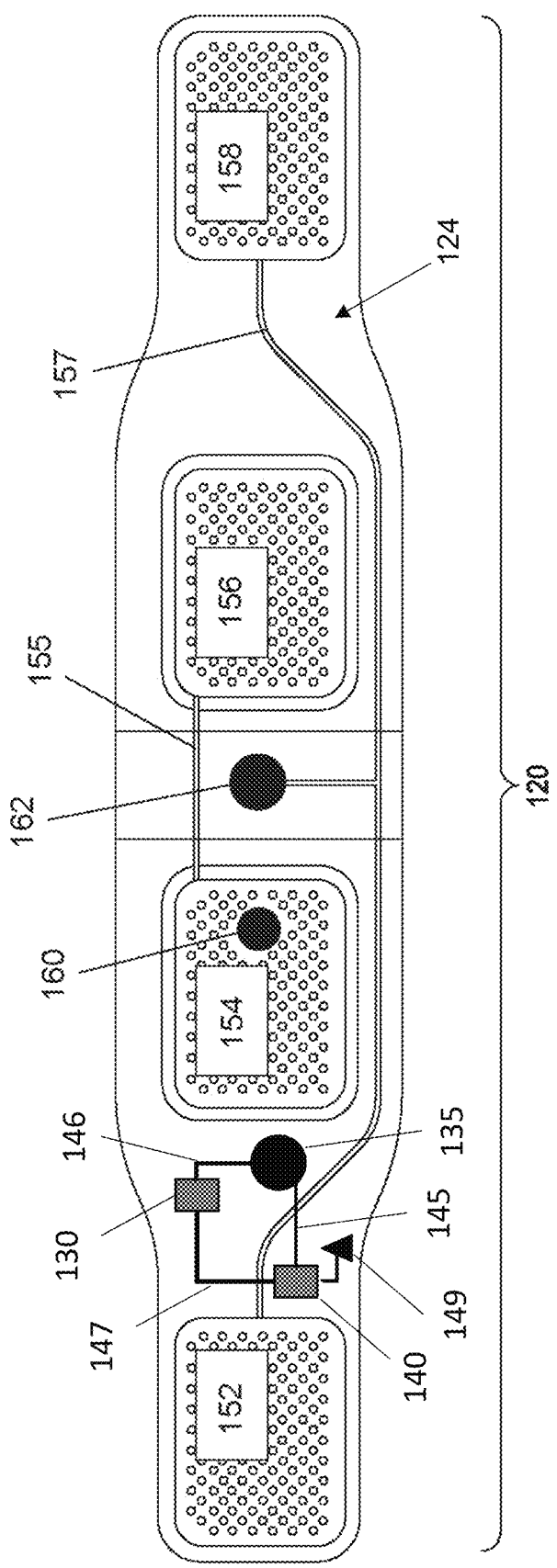
FIG. 3 is a schematic view showing the novel "smart" electrode assembly of FIGS. 1 and 2 in greater detail.

FIG. 3 shows a schematic view of one preferred embodiment of smart electrode assembly 120. Smart electrode assembly 120 preferably comprises a layer of supporting material 124. Supporting material 124 is a flexible, non-conducting structure which essentially behaves as a substrate for carrying the remaining components of smart electrode assembly 120. By way of example but not limitation, supporting material (i.e., substrate) 124 may comprise a sheet of Mylar®.

Smart electrode assembly 120 comprises a plurality of hydrogel electrode pads mounted to supporting material 124, with at least one of the hydrogel electrode pads acting as the cathode electrode for TENS stimulator 105 and at least one of the hydrogel electrode pads acting as the anode electrode for TENS stimulator 105. In one preferred form of the invention, four discrete electrodes 152, 154, 156, 158, each comprising a hydrogel electrode pad and each having an equal or similar size (i.e., an equal or similar size surface area) are provided.

Electrodes 152, 154, 156, 158 are preferably connected in pairs so that electrodes 154 and 156 (representing the cathode electrode of TENS device 100) are electrically connected to one another (e.g., via connector 155), and so that electrodes 152 and 158 (representing the anode electrode of TENS device 100) are electrically connected to one another (e.g., via connector 157). It should be appreciated that electrodes 152, 154, 156, 158 are preferably appropriately sized, and connected in pairs, so as to ensure adequate skin coverage regardless of the rotational position of TENS device 100 (and hence regardless of the rotational position of smart electrode assembly 120) on the leg (or other anatomical location) of a user.

Smart electrode assembly 120 preferably also comprises a sensing unit 130 mounted to supporting material (i.e., substrate) 124. Sensing unit 130 preferably comprises one or more sensors for sensing temperature, moisture, galvanic skin response, chemical monitoring, etc.

And smart electrode assembly 120 preferably also comprises a digital unit 140 mounted to supporting material (i.e., substrate) 124. Digital unit 140 comprises one or more IC components for storing data from sensing unit 130. The IC components of digital unit 140 also contain information that specifies characteristics of smart electrode assembly 120 such as gel pad material type and geometric dimensions, manufacture date, electrode identification number, etc.

In addition, smart electrode assembly 120 preferably also comprises a communication unit 135 which contains electrical components which enable the transmission of data in sensing unit 130 and digital unit 140 to TENS stimulator 105 (and, if desired, enables TENS stimulator 105 to send instructions, new data, etc. to sensing unit 130 and/or digital unit 140).

In one preferred form of the invention, sensing unit 130 communicates with communication unit 135 via a communication link 146, and digital unit 140 communicates with communication unit 135 via a communication link 145. Communications between sensing unit 130 and digital unit 140 are preferably carried out through a communication link 147.

Although the communication links 145, 146, and 147 are visualized in FIG. 3 as line connections, the actual communication links between the connected components can be wireless if desired.

Digital unit 140 may, optionally, contain a power source 149 (such as a button battery) to enable digital unit 140 and sensor unit 130 to operate when smart electrode assembly 120 is not connected to TENS stimulator 105.

In the preferred embodiment shown in FIG. 3, sensing unit 130 and digital unit 140 are placed on the same side of the supporting material (i.e., substrate) 124 as that for the one or more hydrogel electrode pads (i.e., electrodes) 152, 154, 156, 158. It should be appreciated, however, that sensing unit 130 and digital unit 140 can be placed on the opposite side of supporting material 124 if desired. Communication unit 135 can be placed on the same side of supporting material 124 as the other elements connectable to TENS stimulator 105.

It should be appreciated that, in the preferred form of the invention, electrodes 152, 154, 156, 158 are not connected in an interleaved fashion, but rather are connected so that the two inside electrodes 154, 156 are connected to one another, and so that the two outside electrodes 152, 158 are connected to one another. This electrode connection pattern ensures that if the two outer electrodes 152, 158 should inadvertently come into contact with one another, an electrical short of the stimulation current flowing directly from cathode to anode will not occur (i.e., the electrode connection pattern ensures that the therapeutic TENS current is always directed through the tissue of the user).

Electrical current (i.e., for therapeutic electrical stimulation to the tissue) is provided to the electrode pairs 154, 156 and 152, 158 by connectors 160, 162 (FIG. 3) which mate with complementary connectors 210, 212 (FIG. 4), respectively, on TENS stimulator 105. TENS stimulator 105 generates electrical currents that are passed through electrodes 154, 156 and electrodes 152, 158 via connectors 160, 162, respectively.

In one preferred embodiment of the present invention, the skin-contacting conductive material of electrodes 152, 154, 156, 158 is a hydrogel material which is "built into" electrodes 152, 154, 156, 158. In other words, in one preferred form of the invention, electrodes 152, 154, 156, 158 each comprise hydrogel electrode pads. The function of the hydrogel material on the electrodes is to serve as an interface between the electrodes 152, 154, 156, 158 and the skin of the user (i.e., within, or adjacent to, or proximal to, the portion of the user's body in which the sensory nerves which are to be stimulated reside). Other types of electrodes such as dry electrodes and non-contact stimulation electrodes have also been contemplated and are considered to be within the scope of the present invention.

Figure 4:
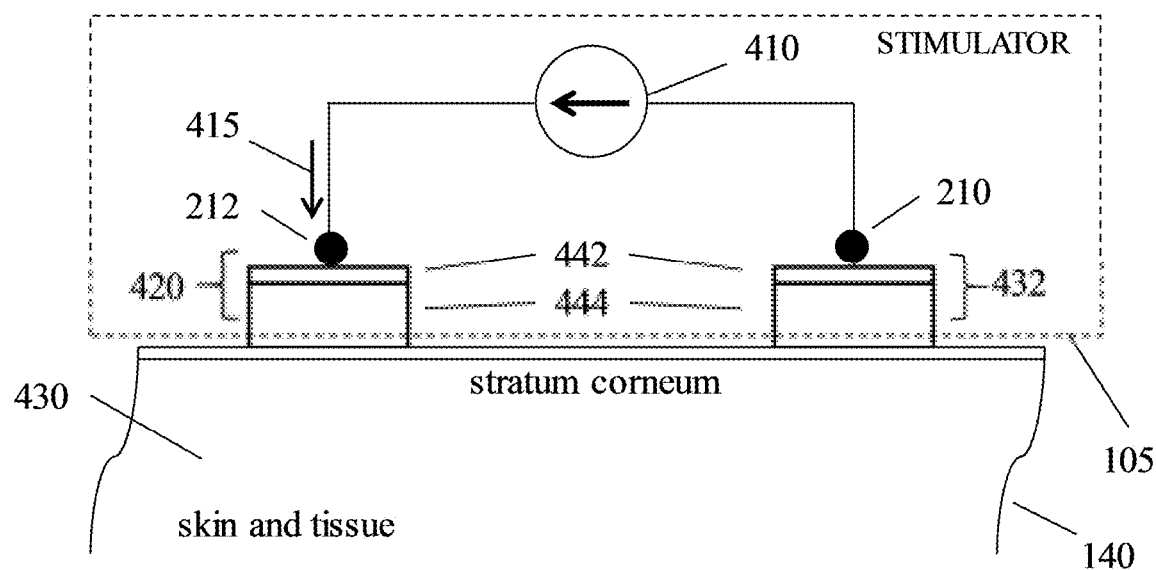
FIG. 4 is a schematic view of the TENS stimulator and the electrode-skin interface of the novel TENS device of FIGS. 1-3.

FIG. 4 is a schematic representation of the current flow between TENS device 100 and the user. As seen schematically in FIG. 4, stimulation current 415 from a constant current source 410 flows into the user's tissue 430 (e.g., the user's upper calf) via an anode electrode 420 (which anode electrode 420 comprises the aforementioned electrodes 152, 158). Anode electrode 420 comprises a conductive backing (e.g., silver hatch) 442 and hydrogel 444, wherein the conductive backing and hydrogel are disposed on supporting material (i.e., substrate) 124. In other words, each of the electrodes 152, 158 comprises a hydrogel electrode pad disposed on supporting material (i.e., substrate) 124. The current passes through the user's tissue 430 and returns to constant current source 410 through cathode electrode 432 (which cathode electrode 432 comprises the aforementioned electrodes 154, 156). Cathode electrode 432 also comprises a conductive backing 442 and hydrogel 444, wherein the conductive backing and hydrogel are disposed on supporting material (i.e., substrate) 124. In other words, each of the electrodes 154, 156 comprises a hydrogel electrode pad disposed on supporting material (i.e., substrate) 124. Constant current source 410 preferably provides an appropriate biphasic waveform (i.e., biphasic stimulation pulses) of the sort well known in the art of TENS therapy. In this respect it should be appreciated that the designation of "anode" and "cathode" electrodes is purely notational in the context of a biphasic waveform (i.e., when the biphasic stimulation pulse reverses its polarity in its second phase of the biphasic TENS stimulation, current will be flowing into the user's body via "cathode" electrode 432 and out of the user's body via "anode" electrode 420).

Figure 5:
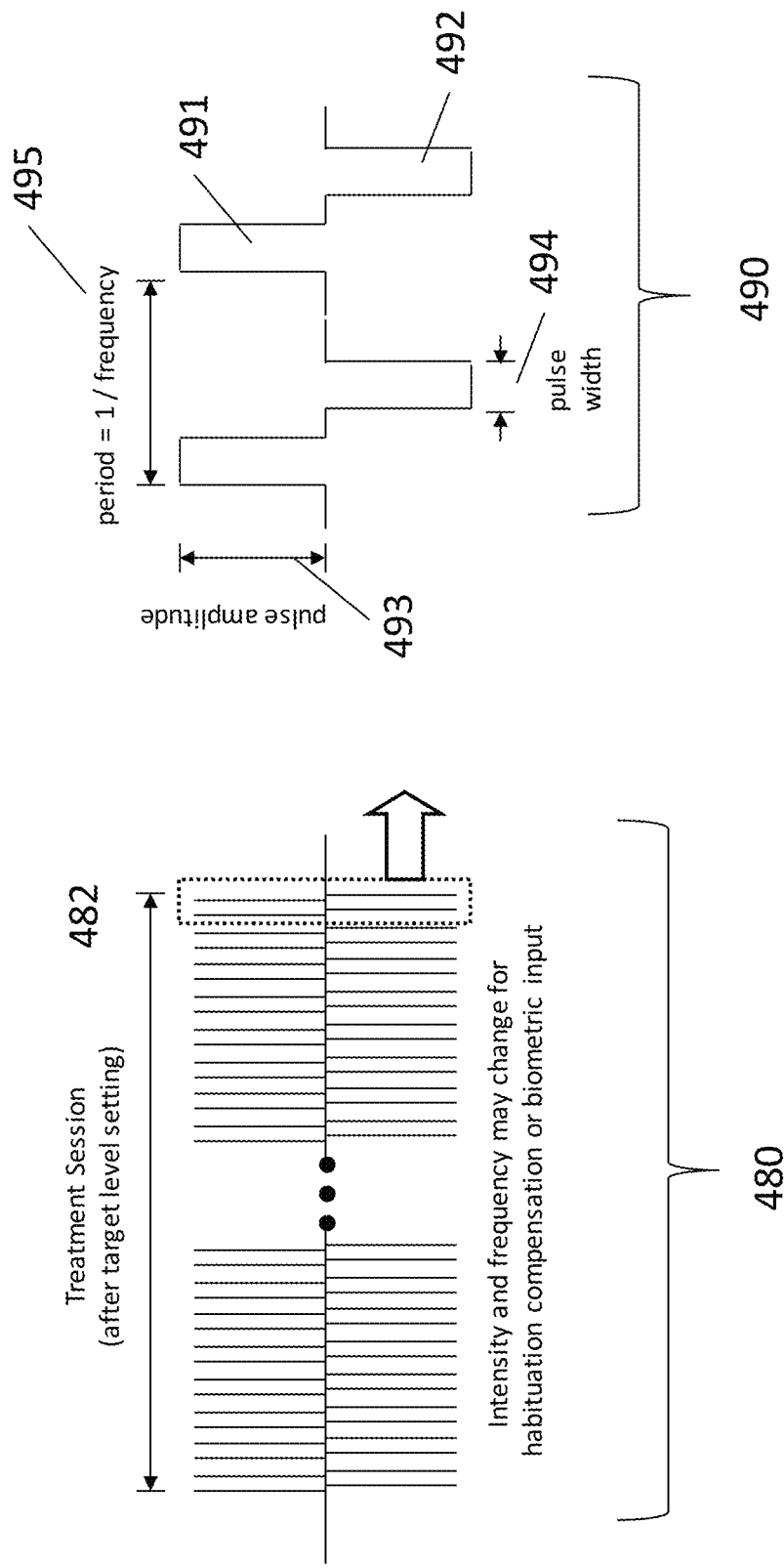
FIG. 5 is a schematic view showing an exemplary electrical stimulation pulse train generated by the TENS stimulator of the novel TENS device of FIGS. 1-4.

FIG. 5 is a schematic view showing a pulse train 480 provided by TENS stimulator 105 during a TENS therapy session 482, and the waveform 490 of two individual biphasic pulses, wherein each individual biphasic pulse comprises a first phase 491 and a second phase 492. In one form of the invention, each pulse waveform is charge-balanced across the two phases 491 and 492 of the biphasic pulse, which prevents iontophoretic build-up under the electrodes of smart electrode assembly 120 that can lead to skin irritation and potential skin damage. In another form of the invention, the individual pulses are unbalanced across the two phases of the biphasic pulse, however, charge-balancing is achieved across multiple consecutive biphasic pulses. Pulses of fixed or randomly-varying frequencies are applied throughout the duration of the therapy session 482. The intensity of the stimulation (i.e., the amplitude 493 of the current delivered by TENS stimulator 105) is adjusted in response to user input and for habituation compensation, as will hereinafter be discussed in further detail.

In order to deliver consistently comfortable and effective pain relief to a user throughout both the day and the night, it may not be appropriate to deliver a fixed TENS stimulation level, since the effect of circadian or other time-varying rhythms can mitigate the effectiveness of TENS stimulation. Parameters impacting TENS stimulation effectiveness include, but are not limited to, stimulation pulse amplitude 493 and pulse width 494, pulse frequency 495, and therapy session duration 482. By way of example but not limitation, higher amplitude and longer pulses (i.e., larger pulse charges) increase the stimulation delivered to the user (i.e., increase the stimulation "dose"), whereas shorter therapy sessions decrease the stimulation delivered to the user (i.e., decrease the stimulation "dose"). Clinical studies suggest that pulse charge (i.e., pulse amplitude and pulse width) and therapy session duration have the greatest impact on the therapeutic stimulation delivered to the user (i.e., the therapeutic stimulation "dose").

Figure 6:
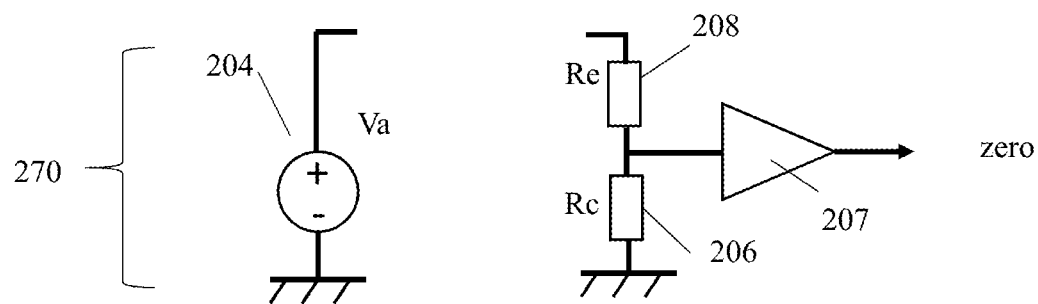
FIG. 6 is a schematic view showing the on-skin detection system of the TENS device shown in FIGS. 1-5, as well as its equivalent circuits when the TENS device is on and off the skin of a user.
Figure 6:
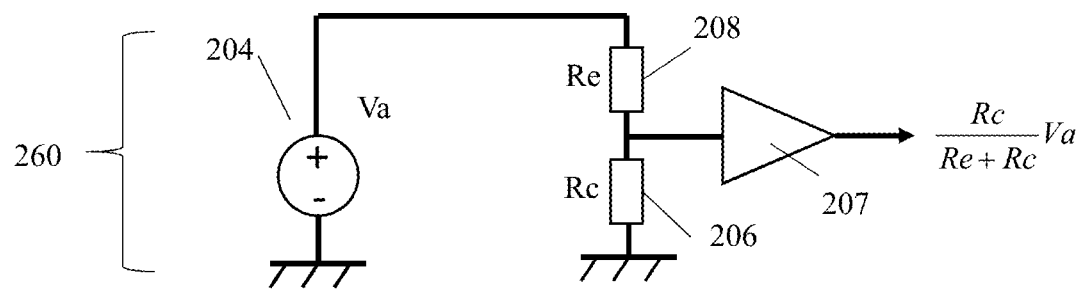
Figure 6:
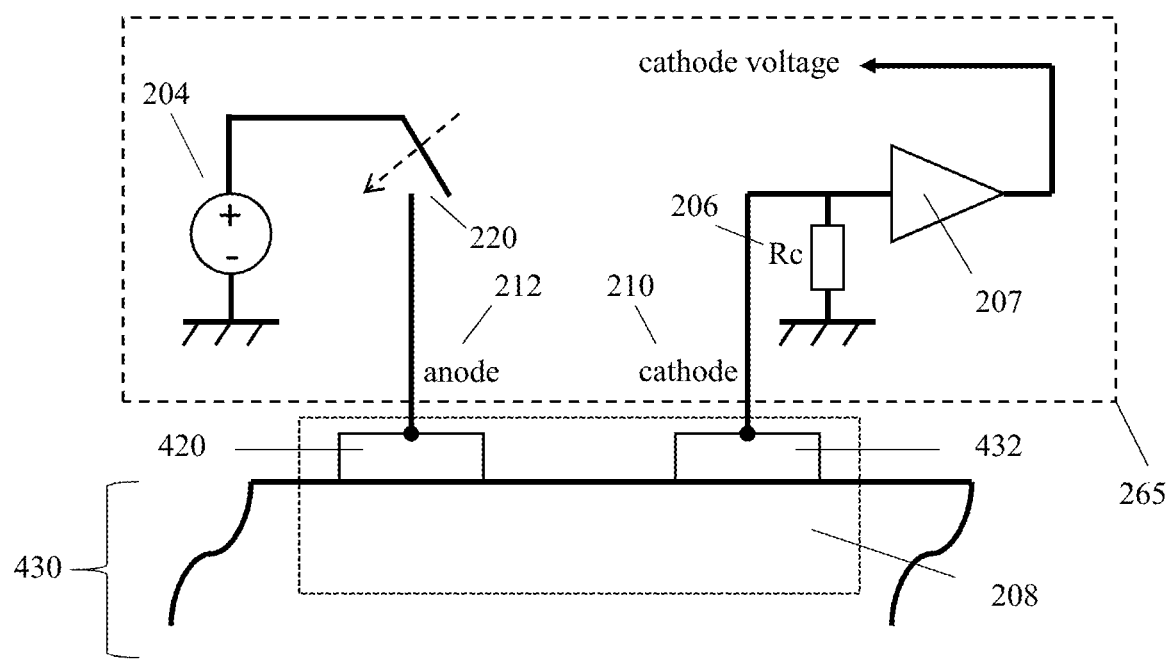

Looking now at FIG. 6, an on-skin detector 265 may be incorporated in TENS device 100 to determine the on-skin time of the smart electrode assembly. On-skin time is defined as the time duration in which the smart electrode assembly is in contact with the skin, whether or not the therapeutic stimulation current is being delivered through the electrodes to the user. More particularly, a voltage of 20 volts from voltage source 204 is applied to the anode terminal (connector 212) of TENS stimulator 105 by closing the switch 220. If the TENS device is worn by the user, then user tissue 430, interposed between anode electrode 420 and cathode electrode 432, will form a closed circuit to apply the voltage to the voltage divider circuit formed by resistors 208 and 206. More particularly, when TENS device 100 is on the skin of the user, the equivalent circuit 260 shown in FIG. 6 represents the real-world system and equivalent circuit 260 allows the anode voltage Va (from voltage source 204) to be sensed through the voltage divider resistors 206 and 208. The cathode voltage measured from the amplifier 207 will be non-zero and close to the anode voltage (from voltage source 204) when TENS device 100 is secured to the skin of the user. On the other hand, when TENS device 100 is not secured to the skin of the user, the equivalent circuit 270 represents the real-world system and the cathode voltage from amplifier 207 will be zero.

Communications Between the Smart Electrode Assembly and the TENS Stimulator

Figure 7:
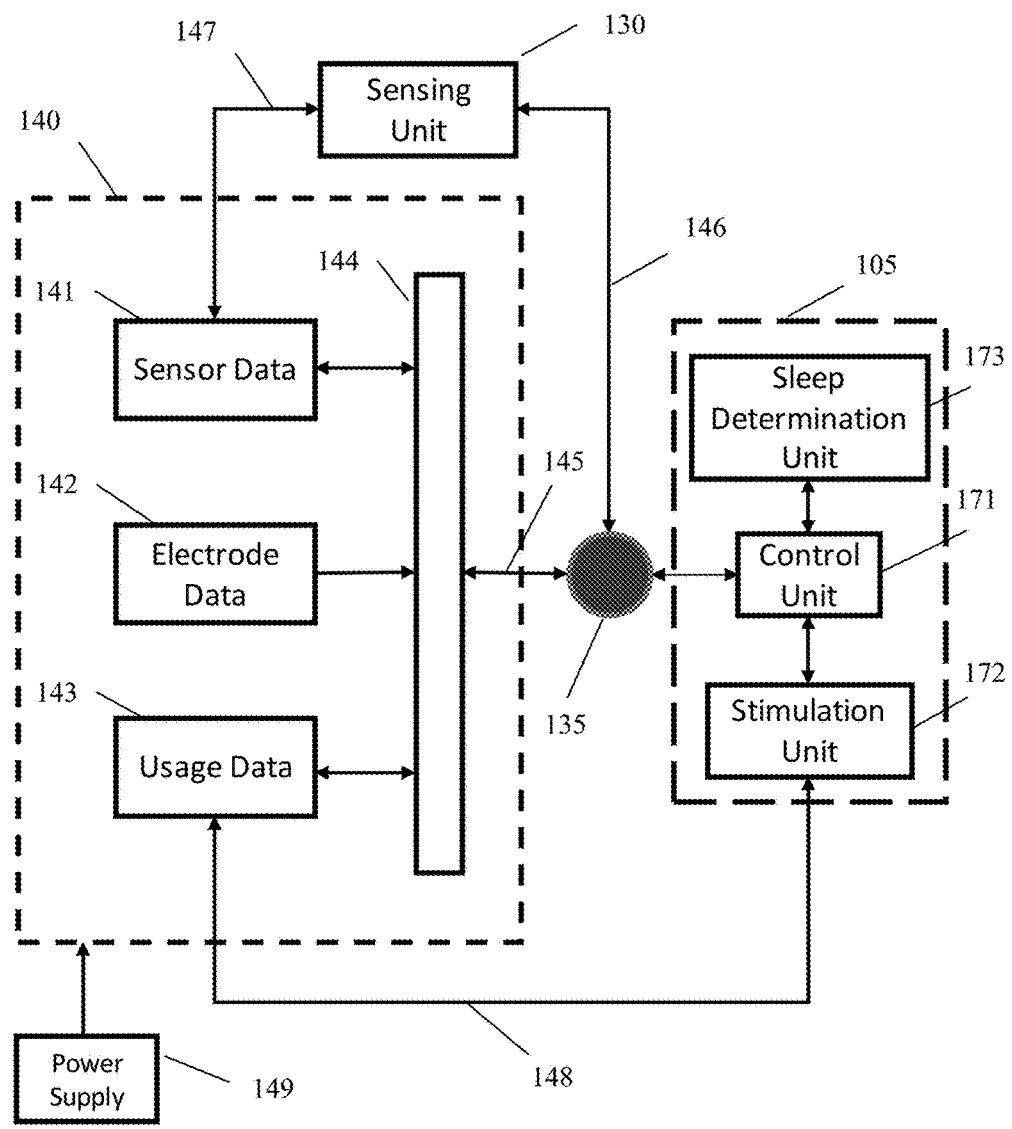
FIG. 7 is a schematic view showing the data storage and communication links between the "smart" electrode assembly and the TENS stimulator.

Looking now at FIG. 7, TENS stimulator 105 comprises a control unit 171 and a stimulation unit 172. Control unit 171 comprises an appropriately-programmed microprocessor which controls operation of stimulation unit 172, whereby to regulate the stimulation current applied to the user by TENS stimulator 105. It will be appreciated that control unit 171 communicates with various components of TENS device 100 so as to apply appropriate TENS therapy to the user, e.g., control unit 171 communicates with user interface elements 106, 108, hand-held electronic device 860, on-skin detector 265, etc.

In accordance with the present invention, and as will hereinafter be discussed, control unit 171 communicates with communication unit 135 of smart electrode assembly 120, whereby to enable control unit 171 to communicate with sensing unit 130 and digital unit 140.

More particularly, information about smart electrode assembly 120 (such as electrode type and manufacture origin) is stored on smart electrode assembly 120 in a digital storage unit 142 of digital unit 140. Digital storage unit 142 may comprise a non-volatile memory circuit such as ROM (i.e., read-only memory). Data from sensing unit 130 (such as data from a temperature sensor) is stored on smart electrode assembly 120 in a digital storage unit 141 of digital unit 140. Digital storage unit 141 may comprise flash memory. Usage data (such as the "time stamp" of the first use of a given smart electrode assembly 120) is stored on the smart electrode assembly in a digital storage unit 143 of digital unit 140. Digital storage unit 143 may comprise RFID (radio frequency ID) tags and one-wire devices.

The information stored in digital unit 140 is communicated between smart electrode assembly 120 and control unit 171 of TENS stimulator 105 via communications unit 135. More particularly, in one preferred form of the invention, communication link 145 (which can be an implementation of industry standard communication protocols developed for the specific digital storage units 141, 142 and 143 of digital unit 140) communicates with digital storage units 141, 142 and 143 through a common interface (or bus) 144, and communication link 145 communicates with communications unit 135.

Additionally and/or alternatively, stimulation unit 172 of TENS stimulator 105 can communicate with the usage data in digital storage unit 143 of digital unit 140 directly via a communication channel 148.

Information from sensing unit 130 (incorporated in smart electrode assembly 120) is transmitted directly to control unit 171 via communication link 146 and communication unit 135, such as through a one-wire communication protocol. Wireless communication links such as RFID protocols can also be employed. Information from sensing unit 130 can also be stored on smart electrode assembly 120 in digital storage unit 141 of digital unit 140 via communication channel 147, without the need to connect smart electrode assembly 120 to TENS stimulator 105. This is particularly useful for smart electrode features like monitoring the storage environment conditions when the smart electrode assembly is not in use (i.e., when the smart electrode assembly is not connected to TENS stimulator 105). Power supply 149 (such as a button battery carried by smart electrode assembly 120) may be provided to enable smart electrode functionalities when the smart electrode assembly is not connected to TENS stimulator 105.

In one preferred form of the invention, smart electrode assembly 120 is designed to communicate with TENS stimulator 105 connected to the smart electrode assembly only through an encryption protocol. In another form of the invention, a subset of the information contained in sensing unit 130 and/or digital unit 140 can be communicated to TENS stimulator 105 in an unencrypted protocol. In yet another form of the invention, a subset of the information contained in sensing unit 130 and/or digital unit 140 of smart electrode assembly 120 can be read by any "readers" but can only be modified by TENS stimulator 105 through an encryption protocol.

TENS Stimulation Control Based on Electrode Type

In one preferred form of the invention, a common mechanical and electrical connection interface is provided between TENS stimulator 105 and a series of smart electrode assemblies 120, wherein each smart electrode assembly may have different characteristics. In this form of the invention, control unit 171 of TENS stimulator 105 is configured to determine the type of smart electrode assembly 120 connected to TENS stimulator 105 based on information stored on the smart electrode assembly.

In one preferred form of the invention, information about the electrode type of the smart electrode assembly is encoded in an integrated circuit (IC) chip (i.e., digital storage 142 of digital unit 140) that can be read by TENS stimulator 105 through communication protocols like 1-wire, I2C, or RFID. If the smart electrode assembly cannot be recognized, or if the smart electrode assembly does not belong to a set of supported smart electrode assemblies, TENS stimulator 105 may treat the electrode assembly as a special type of electrode assembly with a default set of characteristics.

In another form of the invention, TENS stimulator 105 may terminate electrical stimulation of the user when the electrode type is not recognized.

In yet another form of the invention, TENS stimulator 105 may cease to function until a specific smart electrode assembly is connected.

In yet another form of the invention, if the electrode type is not recognized, TENS stimulator 105 may cease to function until the TENS stimulator is reset by the manufacturer.

In one preferred form of the invention, feedback (such as a blinking LED) is provided to the user when the electrode array is not recognized by TENS stimulator 105.

In another form of the invention, when the electrode assembly is not recognized by TENS stimulator 105, no feedback is provided to the user other than that certain functionalities of TENS stimulator 105 have become unavailable to the user.

One aspect of electrode type is the gel characteristics of the hydrogel electrode pad. By way of example but not limitation, sweat-resistant gel absorbs less moisture and is therefore suitable for use during outdoor activities in humid weather. Standard gel contains more water to provide consistent and comfortable interface for everyday use. Because of the moisture content level of the gel in the hydrogel electrode pad, each type of electrode will have different electrode-skin interface characteristics when the hydrogel electrode pad is placed on the skin of the user. A higher electrode-skin interface impedance is expected from the hydrogel electrode pad which utilizes a sweat-resistant gel type.

In one form of the invention, based on the electrode gel type, control unit 171 of TENS stimulator 105 is configured to set the stimulation parameters of TENS stimulator 105 accordingly to compensate for the impedance difference of different gel types.

In addition to stimulation parameter adjustments, TENS stimulator 105 is also configured to adaptively predict the usage parameters. In one preferred form of the invention, remaining battery capacity (in terms of the number of therapy sessions available) is calculated and reported to the user based on the usage history of a standard gel type electrode. If a smart electrode assembly having electrodes with sweat-resistant gel is detected, the battery capacity (expressed in the number of therapy sessions available) can be adaptively adjusted to a smaller number due to the expected higher impedance of the sweat-resistant gel without accumulating actual usage history for the new gel type.

Another aspect of electrode type is the size of the hydrogel electrode pads. Given the same stimulation current intensity, smaller electrode-skin contact area will evoke a stronger sensation of the stimulation due to a higher current density (defined as current intensity divided by the contact area). If a user has calibrated their TENS stimulator to a particular level of stimulation intensity with a given smart electrode assembly having a particular electrode size, and then later switches to a smart electrode assembly 120 having a smaller electrode size, control unit 171 of TENS stimulator 105 is configured to automatically reduce the stimulation intensity to avoid producing an uncomfortable sensation for the user due to a too-strong stimulation density (i.e., due to the reduced electrode-skin contact area of the smaller electrodes of the new smart electrode assembly). Similar adjustments can be made when the user changes electrode type from a smart electrode assembly with smaller size hydrogel electrode pads to one with larger size hydrogel electrode pads to maintain the same stimulation sensation.

Another aspect of electrode type is the class of electrodes. As an example, different countries or regions may have different requirements for the electrodes. Those requirements may not be functional and could be just labeling. The same TENS stimulator can be distributed to multiple regions while still complying with regulatory requirements. To ensure that TENS stimulator 105 will "lock onto" (i.e., adapt to correctly function with) a specific class of electrodes, the TENS stimulator may be configured to operate with only a single class of smart electrode assemblies. When TENS stimulator 105 is connected to an electrode assembly of a class supported by the TENS stimulator, the TENS stimulator may be configured to automatically reduce its support class type to that specific class of the smart electrode assembly connected to the TENS stimulator. Any electrode assembly of a different class will prevent the TENS stimulator from delivering electrical stimulation through that electrode assembly. Additionally, auxiliary functions of the TENS stimulator, such as activity tracking and sleep monitoring, may also be disabled upon connecting to an electrode assembly of a class type different from the class type of the first-connected electrode assembly.

Electrode Usage Tracking

In one preferred form of the invention, the electrodes of smart electrode assembly 120 are preferably made of hydrogel-based materials. The adhesive and conductive properties of electrodes utilizing hydrogel-based materials degrade with usage and time. It is, therefore, advisable to replace smart electrode assemblies 120 based on usage time duration and interval. Usage time duration is the accumulative time the smart electrode assembly 120 is in contact with skin of the user. Usage interval is the elapsed time between the current time and the time of the first use of a smart electrode assembly.

With the prior art, a replacement schedule is often communicated to the user as a fixed usage interval, such as that the TENS electrodes should be replaced after every two weeks of usage interval. Such a fixed usage interval recommendation is generally based on a typical daily usage period under typical user conditions. This may lead to sub-optimal therapeutic results for some users whose electrode quality degenerates faster than that for the typical use conditions. Similarly, the fixed replacement schedule may cause some electrodes to be replaced sooner than necessary.

Accordingly, in one preferred form of the invention, smart electrode assembly 120 uses digital storage unit 143 (in digital unit 140) to store total usage time. The stored time is initialized to zero for new smart electrode assemblies at the time of manufacture. When the smart electrode assembly is thereafter connected to TENS stimulator 105 and placed "on skin", control unit 171 of TENS stimulator 105 will start tracking usage time for that smart electrode assembly. TENS stimulator 105 then updates digital storage unit 143 on smart electrode assembly 120 with the accumulative on-skin time. This update is preferably done at a pre-determined time interval. In one preferred embodiment, the update interval is one minute.

For a therapy session of 60 minutes, the total usage time for smart electrode assembly is incremented by 60 minutes. Optionally, the duration of a therapy session is modified by a factor proportional to the stimulation current intensity passing through the smart electrode assembly. The modified duration is then added to the total usage time. Additionally, on-skin time without active electrical stimulation can also be added to the total usage time with a different (e.g., lesser) modification factor. In another form of the invention, digital unit 140 comprises electronics to track on-skin time of the smart electrode assembly 120 so that the total usage time of the smart electrode assembly is accurately tracked with or without connection to the TENS stimulator 105.

In one preferred form of the invention, two distinct threshold values are set for total usage time. One threshold value is used to initiate a reminder (Threshold4Reminder1) to replace the smart electrode assembly and the other threshold value (Threshold4Unusable1) is used to mark that the smart electrode assembly is unusable. When the total usage time exceeds the Threshold4Reminder1 threshold value, TENS stimulator 105 is configured to initiate a user feedback to remind the user to replace the smart electrode assembly. The threshold values can be set and stored on the smart electrode assembly at different locations of the same digital storage unit 143. The threshold value can also be set by the user on TENS stimulator 105 or through an APP on a device (e.g., hand-held electronic device 860) connected to the TENS stimulator. In one preferred form of the invention, the feedback to the user is in the form of a sequence of electrical pulses which have a pattern distinct from the pattern of normal therapy pulses. In another form of the invention, user feedback comprises a mechanical vibration. In yet another form of the invention, the user feedback is through a connected APP to display a visual or audio reminder on a device (e.g., hand-held electronic device 860) connected to the TENS stimulator.

When the total usage time exceeds the Threshold4Unusable1 threshold, TENS stimulator 105 updates a status value stored on digital storage unit 143. Once the status is updated to "unusable", no further electrical stimulation will be delivered through this particular smart electrode assembly by TENS stimulator 105. In one preferred form of the invention, the threshold value Threshold4Unusable1 is 20 hours larger than the threshold value Threshold4Reminder1, and the threshold Threshold4Reminder1 has a value of 200 hours.

In one preferred form of the invention, the usage interval of each smart electrode assembly 120 is tracked similar to that of usage time. Upon first connection with TENS stimulator 105, the "date stamp" (or its equivalent) of the first-time use of a smart electrode assembly 120 is stored in digital storage unit 143 incorporated in that smart electrode assembly. The total usage interval is updated based on the current "date stamp" and the first-time use "date stamp". The total usage interval is compared with an alert threshold value (Threshold4Reminder2) stored in digital unit 140 of the smart electrode assembly. If the total usage interval is greater than the alert threshold, an alert is issued to the user for electrode replacement. The total usage interval is compared with a maximum usage interval threshold (Threshold4Unusable2). If the total usage interval is greater than the maximum usage interval threshold, TENS stimulator 105 marks that smart electrode assembly as unusable.

In one preferred form of the invention, the alert for smart electrode assembly replacement (trigged by either usage duration or usage interval) automatically generates an order with a supplier for a specified type and class of smart electrode assembly.

Storing the usage information on the smart electrode assembly itself, instead of storing usage information on TENS stimulator 105, has some advantages. When a user has two TENS stimulators and uses them interchangeably (e.g., during recharging of device A, device B is used for TENS therapy), each stimulator will only "see" a portion of the electrode usage history. By storing usage information on the smart electrode assembly itself, it overcomes the incomplete usage history seen by each of the multiple stimulators.

Moisture Condition Tracking

In one preferred form of the invention, a moisture sensor (carried by sensing unit 130) monitors the dryness of the skin of the user at the location where smart electrode assembly 120 is in contact with the skin. Dry skin depletes the water in the hydrogel electrode pads more quickly than normal skin. Loss of water in the hydrogel electrode pads makes the gel pads less conductive and, therefore, would require more frequent replacement of the smart electrode assembly. The results of monitoring of skin dryness are used by TENS stimulator 105 to modify one or more values used to prompt users (e.g., via hand-held electronic device 860) for electrode replacement. Values include usage duration reminder threshold (Threshold4Reminder1), usage duration unusable threshold (Threshold4Unusable1), usage interval threshold (Threshold4Reminder2), and usage interval threshold (Threshold4Unusable2).

When a smart electrode assembly 120 is not placed on the skin of a user, its hydrogel electrode pads may be exposed to the elements of the storage environment. In one preferred form of the invention, a moisture sensor (carried by sensing unit 130) monitors the humidity of the environment where the smart electrode assembly is stored. Monitored ambient conditions are used by control unit 171 of TENS stimulator 105 to modify one or more values stored in digital storage unit 141 of smart electrode assembly 120. Values include the usage interval threshold (Threshold4Reminder2) and the usage interval threshold (Threshold4Unusable2). In another form of the invention, feedback is provided to the user (e.g., via hand-held electronic device 860) to recommend that the smart electrode assembly be stored in a more controlled environment when monitored ambient humidity conditions are expected to adversely impact the electrode conditions. Examples of such a more controlled environment include a sealed bag to prevent excessive moisture loss from the hydrogel electrode pads.

Skin Temperature Tracking

Skin temperature changes are correlated with several physiological changes relevant to TENS stimulation. These include: temperature changes due to an increase in local blood flow as a result of electrical stimulation; temperature changes coinciding with sleep onset; and temperature fluctuations during various sleep stages. Clinical research also reports benefits of improved sleep outcome with the warming of a lower extremity. A skin-contact temperature sensor provided in sensing unit 130 of smart electrode assembly 120 can provide the precise skin temperature measurements needed to detect small changes in skin temperature associated with the aforementioned physiological changes.

It is known that electrical stimulation increases local blood flow. In one preferred form of the invention, the temperature sensor in sensing unit 130 of smart electrode assembly 120 monitors skin temperature. Monitored skin temperature results are used by control unit 171 of TENS stimulator 105 to determine the effect of the electrical stimulation. In one preferred form of the invention, the skin temperature at the onset of stimulation or immediately prior to stimulation is measured ($T_1$). After a fixed time period of TENS stimulation, e.g., 10 minutes, the skin temperature is measured again ($T_2$). If the temperature change ($dT = T_2 - T_1$) falls within a target range, e.g., 0.25 to 0.75 degree Celsius, then the TENS stimulation may be considered to be effective. If the temperature change dT is close to zero, then the TENS stimulation may be considered to be below a target intensity and control unit 171 may prompt the user (e.g., via hand-held electronic device 860) to increase the TENS stimulation intensity. If the change dT is too large, the stimulation intensity may be too strong and control unit 171 of TENS stimulator 105 may prompt the user (e.g., via hand-held electronic device 860) to reduce the TENS stimulation intensity.

In another form of the invention, adjustment of the stimulation intensity based on temperature change (dT) is made automatically by control unit 171 of TENS stimulator 105.

In one preferred form of the invention, the aforementioned threshold value is a fixed value.

In another form of the invention, the aforementioned threshold value is a function of the skin moisture level and the skin temperature at the baseline ($T_1$).

In one preferred form of the invention, temperature change is also used to determine whether the TENS stimulation intensity is above an electro-tactile threshold. The electro-tactile threshold is the lowest stimulation current intensity that evokes an electro-tactile sensation of the user receiving the stimulation. The electro-tactile threshold has been used to set an optimal TENS stimulation intensity $I_T$ that evokes a strong but comfortable sensation. When a user incorrectly identifies a threshold which is higher than the true electro-tactile threshold, therapeutic stimulation intensity based on the identified threshold will be set too high.

In one preferred form of the invention, skin temperature ($T_b$) is measured before any TENS stimulation current is delivered to the body via the smart electrode assembly. The stimulation current is then increased in a step-wise fashion to allow the user to identify the electro-tactile sensation threshold. Once the user identifies an electro-tactile sensation threshold, control unit 171 of TENS stimulator 105 stimulates the user at that intensity level for a period of time (e.g., 10 minutes). If the measured skin temperature Ts is higher than ($T_b$+0.5) degree Celsius, the intensity indicated by the user is considered to be higher than the true electro-tactile sensation threshold. Control unit 171 of TENS stimulator 105 will then prompt the user (e.g., via hand-held electronic device 860) to repeat the process of identifying the proper electro-tactile threshold.

In another form of the invention, the identified threshold is considered to be higher than the true electro-tactile threshold level when the measured skin temperature Ts is higher than ($T_b$+0.5) degree Celsius and muscle twitches under the electrode-skin contact area are detected by the TENS stimulator (e.g., via an accelerometer carried in sensing unit 130, or via an accelerometer carried by TENS stimulator 105).

Skin temperature is known to fluctuate throughout the day. The nerve activation threshold (and thus the electro-tactile threshold) is known to be temperature dependent—the activation threshold is lower when the skin temperature is higher. Therefore, a TENS stimulation intensity optimized under one skin temperature condition will need to be adjusted when the skin temperature changes. In one preferred form of the invention, the skin temperature $T_C$ monitored by sensing unit 130 on smart electrode assembly 120 is used by control unit 171 of TENS stimulator 105 to adjust the stimulation intensity $I_O$ determined under a different temperature condition $T_O$. If the current skin temperature $T_C$ is higher than the original temperature $T_O$, control unit 171 of TENS stimulator 105 adjusts the stimulation intensity $I_O$ with a negative offset. Similarly, if the current skin temperature $T_C$ is lower than the original temperature $T_O$, control unit 171 of TENS stimulator 105 adjusts the stimulation intensity $I_O$ with a positive offset.

Chronic pain can interfere with sleep and poor sleep can worsen the pain. Recent technological advances have made it possible for users with chronic pain to use TENS devices during sleep by overcoming safety issues which prevented other TENS devices from being used during sleep. A temperature sensor contained in sensing unit 130 of smart electrode assembly 120 can monitor skin temperature patterns when the user is asleep at night.

In one preferred form of the invention, the skin temperature is monitored during sleep. A TENS stimulator comprising an embedded accelerometer can sense the body orientation and movement to determine the timing of events like going to bed, falling asleep, and waking up. Research has shown that individual sleep onset latency (time between going to bed and falling asleep) can be improved with a temperature manipulation (e.g., by increasing foot temperature such as with footbaths prior to going to bed), but the amount of the temperature manipulation and sleep onset latency improvement varies from subject to subject. With continuous monitoring of skin temperatures and objective sleep onset latency measures, the specific relationship between sleep onset latency and skin temperature can be established for each user (i.e., a target skin temperature range can be established for improved sleep). When measured skin temperature is outside the target range, a prompt may be issued to the user (e.g., via hand-held electronic device 860) when the user first gets in bed.

After falling asleep, individual goes through different sleep stages in a sleep cycle: non-REM (rapid eye movement) stage 1 (NS1); non-REM stage 2 (NS2); non-REM stage 3 (NS3); non-REM stage 2 (NS2); non-REM stage 1 (NS1); and REM sleep (REMS). After REMS, the individual may return to NS1 and repeat another sleep cycle. During non-REM sleep stages, the body temperatures are lower than normal. The body temperature falls to its lowest during REMS stage. A series of body movements usually occurs during the transition from NS3 to NS2. Actigraphy-based sleep monitoring may be able to determine this transition. However, a lack of body movements in other sleep stages makes actigraphy-based sleep monitoring ineffective to identify these sleep stages inasmuch as body movements could also be due to poor sleep or the user being about to get up. Incorporating skin temperature measurements into actigraphy-based sleep monitoring increases sleep monitoring accuracy.

Accordingly, in one preferred form of the invention, temperature sensor measurements (from sensing unit 130) are used in a sleep classification algorithm incorporated in a sleep determination unit 173 incorporated in TENS stimulator 105. Sleep determination unit 173 may be any suitable component capable of determining the sleep status of a user and modifying TENS therapy applied to the user based on the sleep status of the user. By way of example but not limitation, sleep determination unit 173 may be of the sort disclosed in pending prior U.S. patent application Ser. No. 14/253,628, filed Apr. 15, 2014 by Neurometrix, Inc. and Shai Gozani et al. for TRANSCUTANEOUS ELECTRICAL NERVE STIMULATOR WITH AUTOMATIC DETECTION OF USER SLEEP-WAKE STATE, which patent is hereby incorporated herein by reference. This patent application discloses, among other things, determining the sleep status of a user based on the body movement of the user and modifying TENS therapy applied to the user based on the sleep status of the user. After sleep onset is detected by the actigraphy-based sleep algorithm incorporated in the aforementioned sleep determination unit 173, the user enters NS1 and the user's skin temperature is expected to decrease. If body temperature stays low or trends lower, body movement is interpreted as a transition from NS3 to REMS instead of as a precursor for waking up or movement due to chronic pain discomfort. With temperature tracking, performance of the actigraphy-based sleep classification algorithm can be enhanced to discriminate different sleep stages within sleep period.

Thus, previously disclosed apparatus and methods for controlling TENS therapy during sleep based on body movement (see, for example, the aforementioned pending prior U.S. patent application Ser. No. 14/253,628) can be enhanced by using temperature information available from smart electrode assembly 120.

In one preferred form of the invention, if leg movement is coupled with body temperature trending down, then control unit 171 of TENS stimulator 105 will cause TENS therapy stimulation to not be initiated. If leg movement is not coupled with body temperature trending down, then control unit 171 of TENS stimulator 105 will allow TENS therapy stimulation to proceed based on a prior schedule.

In another form of the invention, ambient temperature acquired by a temperature sensor incorporated in TENS stimulator 105 is used to determine sleep quality and to control TENS stimulation. Thermal environment is one of the most important factors that can affect human sleep (Okamoto-Mizuno et al Effects of thermal environment on sleep and circadian rhythm, Journal of Physiological Anthropology, 31:14, 2012). For example, mild cold ambient temperature increases slow wave sleep (NS3 sleep). Associations between sleep quality as determined by actigraphy and thermal environment can be determined for each user and thermal environment conditions that are associated with better sleep quality can be communicated to the user to improve sleep quality.

In another form of the invention, a combination of skin temperature (acquired by a temperature sensor in sensing unit 130 of smart electrode assembly 120) and the ambient temperature determined by a different temperature sensor incorporated in TENS stimulator 105 are used to determine sleep quality. Sleep quality determination results are, in turn, used to modify operation of TENS stimulator 105 via control unit 171. Skin temperature changes are shown to be associated with different sleep stages, and skin temperature changes in the context of ambient temperature conditions can provide a more specific indication of sleep stages and stage-to-stage transition. For example, a decrease in skin temperature under a steady ambient temperature condition is a more accurate predictor of transition from NS3 to REMS sleep stage than the same skin temperature decrease in the presence of a drop in ambient temperature.

Monitoring ambient temperature where the TENS electrode is stored can also provide information regarding the expected quality degradation of the smart electrode assembly. Extreme temperature (too cold or too hot) can cause the hydrogel electrode pads of the smart electrode assembly to lose their conductive properties. Accordingly, in one preferred form of the invention, a temperature sensor in sensing unit 130 of smart electrode assembly 120 tracks environmental temperature when electrode assembly 120 is in storage (i.e., not on skin). The temperature history is read and processed by control unit 171 of TENS stimulator 105 after the smart electrode assembly 120 is connected to TENS stimulator 105. When extreme storage temperatures are detected, the expected usage time remaining for the smart electrode assembly is modified to reflect the adverse impact of ambient temperature on the hydrogel electrode pads of the smart electrode assembly. In another form of the invention, feedback is provided to the user (e.g., via hand-held electronic device 860) to recommend that the smart electrode assembly be stored in a more controlled environment such as an indoor living space.

Galvanic Skin Response Sensor

A galvanic skin response sensor, provided as part of sensing unit 130 of smart electrode assembly 120 measures the skin conductance level or electrodermal activity (EDA) of a user. Such EDA patterns have been shown to be correlated with different stages of sleep. In particular, high frequency activities of EDA often occur in NS2 and NS3 stages of sleep (Sano et al, Quantitative analysis of wrist electrodermal activity during sleep, Int J. Psychophysiol. 94(3): 382-389, 2014).

In one preferred form of the invention, galvanic skin response sensor measurements (from the galvanic skin response sensor provided in sensing unit 130) are used in the sleep classification algorithm as a part of a sleep determination unit 173 incorporated in the TENS stimulator to determine sleep stages. Refined sleep stage determination results are then used by control unit 171 of TENS stimulator 105 to control operations of stimulation unit 172 of TENS stimulator 105.

In another preferred form of the invention, determination results based on accelerometer, temperature, chemical, and galvanic skin response sensors are combined to improve the sleep stage determination outcome.

Electrode Quality Tracking

Properties of smart electrode assembly 120, particularly the impedance and usage durations, can be stored in the smart electrode assembly and analyzed to predict the useful life of the smart electrode assembly before replacement is needed.

In one preferred form of the invention, the electrode history can be summarized in a quality index Q. The properties of the smart electrode assembly are updated and stored in digital storage unit 142 on smart electrode assembly 120 whenever control unit 171 of the TENS stimulator 105 takes a new measurement. The property attributes of measurements include first-time use impedance (impedance measured the very first time the electrode is used on the skin), impedance history (impedance measured during each TENS therapy session), stimulation current intensity used when making impedance measurements, and time stamps of the measurements. An average of the initial five sets of impedance values is calculated as baseline impedance ($IMP_B$). The most recent five sets of impedance values are averaged to obtain current impedance ($IMP_C$). An electrode array quality index is developed to quantify the electrode array condition. In one preferred form of the invention, the quality index Q ranges from 100 (best) to 0 (worst) and is defined as $$100*\exp(-IMP_C/IMP_B+1).$$

Control unit 171 of TENS stimulator 105 uses the quality index Q to modify the stimulation intensity by adding an offset to the original target stimulation intensity level $I_T$. In one preferred form of the invention, the offset is set to be (Q/100−1) dB. As a result of this offset, a lower stimulation intensity level is used when the electrode quality degrades. A lower quality index Q indicates lower conductive and adhesive properties for the hydrogel electrode pads of the smart electrode assembly (the lower adhesive properties can also mean the effective electrode-skin contact area is lower than that from a new smart electrode assembly). If the same stimulation current intensity is used, a higher current density (current intensity divided by electrode-skin contact area) will be passing through the electrode-skin interface, potentially causing discomfort for the TENS user. The quality index Q is also used by the TENS stimulator to modify one or more values stored in the smart electrode assembly to predict the useful life of the electrode assembly. Values include the remaining usage time and the remaining total usage duration of the smart electrode assembly. In one form of the invention, the threshold values are adjusted upwards if the quality index Q is above 80 after 10 days of total usage days. In another form of the invention, the threshold value is adjusted downward if the quality index Q is below 50 within 10 days of total usage days.

In one preferred form of the invention, information stored on the smart electrode assembly is transmitted (either directly or via TENS stimulator 105) to a central database for permanent storage via communication links such as Bluetooth link or wireless link. Such information can be used to identify types of electrode arrays that are more appropriate for the user based on the user's electrode array usage characteristics and history when a new order for electrode arrays is requested by the user. As an example, a user who tends to sweat more during the summer time (as measured by the moisture and temperature sensors of sensing unit 130 of smart electrode assembly 120) may be offered an electrode assembly comprising hydrogel electrode pads made of conductive gel that is less absorbent of water molecules.

Recommender System for Electrode Reorders

In one preferred form of the invention, information collected from multiple smart electrode assemblies used by the same user is transmitted to a central database for permanent storage via communication links such as Bluetooth link or wireless link. Such information can be used to identify electrode assembly types that are more appropriate for the user based on the user's electrode usage characteristics and history. A recommendation can be made to the user when a new order for electrodes is requested from the user. As an example, a user who tends to sweat more during the summer time (as measured by the moisture and temperature sensors of sensing unit 130 of smart electrode assembly 120) may be offered an electrode assembly comprising hydrogel electrode pads made of conductive gel that is less absorbent of water molecules.

MODIFICATIONS OF THE PREFERRED EMBODIMENTS

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. Apparatus for transcutaneous electrical stimulation in a user, said apparatus comprising:
    a stimulation unit for electrically stimulating body tissue of said user using electrical pulses;
    a sensing unit for measuring body temperature of said user; and
    a control unit connected to said stimulation unit and said sensing unit, said control unit being configured to (i) record a first body temperature from said sensing unit before electrical stimulation; (ii) apply electrical stimulation at a first stimulation intensity for a period of time and monitor body temperature change from the first body temperature; (iii) automatically increase the stimulation intensity when the body temperature change is within a temperature change threshold; and (iv) determine an electrotactile sensation stimulation intensity of said user as the lowest stimulation intensity causing the body temperature change to exceed the temperature change threshold.

2. Apparatus according to claim 1 wherein said sensing unit further comprises a storage unit.

3. Apparatus according to claim 2 wherein said storage unit stores at least one of the following: the first body temperature; the electrotactile sensation stimulation intensity; the body temperature under which the electrotactile sensation threshold is determined.

4. Apparatus according to claim 1 wherein a therapeutic stimulation intensity is determined by adding a pre-determined intensity offset to said electrotactile sensation stimulation intensity.

5. Apparatus according to claim 4 wherein the offset is a function of the body temperature.

6. Apparatus according to claim 1 wherein a therapeutic stimulation intensity is determined by multiplying said electrotactile sensation stimulation intensity with a pre-determined factor.

7. Apparatus according to claim 6 wherein the factor is a function of the body temperature.

8. Apparatus for transcutaneous electrical stimulation in a user, said apparatus comprising:
    a stimulation unit for electrically stimulating body tissue of said user using electrical pulses;
    a sensing unit for measuring body temperature of said user;
    a storage unit; and
    a control unit connected to said stimulation unit, said sensing unit, and said storage unit, said control unit being configured to (i) retrieve a therapeutic stimulation intensity and a first temperature from said storage unit; (ii) record a body temperature from said sensing unit before electrical stimulation; (iii) adjust said therapeutic stimulation intensity when the difference between said body temperature and said first temperature exceeds a threshold; (iv) apply electrical stimulation at said adjusted therapeutic stimulation intensity.

9. Apparatus according to claim 8 wherein the threshold is one degree Celsius.

10. Apparatus according to claim 8 wherein adjustment of therapeutic stimulation intensity comprises adjusting at least one of (i) amplitude of the stimulation pulses; (ii) duration of the stimulation pulses; (iii) total charge of the stimulation pulses; and (iv) frequency of the stimulation pulses.

11. Apparatus according to claim 10 wherein amount of therapeutic stimulation intensity adjustment is a function of at least one of the following: (i) the first temperature; and (ii) the body temperature.

12. Apparatus according to claim 8 wherein the storage unit stores the body temperature and adjusted therapeutic stimulation intensity.

13. Apparatus according to claim 8 wherein the control unit modifies therapeutic stimulation intensity based on input from the user.

14. Apparatus according to claim 13 wherein the storage unit stores modified therapeutic stimulation intensity and the body temperature at the time of stimulation intensity modification.

* * * * *